United States Patent
Hay et al.

(10) Patent No.: US 6,720,330 B2
(45) Date of Patent: Apr. 13, 2004

(54) SOMATOSTATIN ANTAGONISTS AND AGONISTS THAT ACT AT THE SST SUBTYPE 2 RECEPTOR

(75) Inventors: Bruce A. Hay, East Lyme, CT (US); Bridget M. Cole, Stonington, CT (US); Anthony P. Ricketts, Stonington, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/953,785

(22) Filed: Sep. 17, 2001

(65) Prior Publication Data

US 2002/0091125 A1 Jul. 11, 2002

Related U.S. Application Data

(60) Provisional application No. 60/249,514, filed on Nov. 17, 2000.

(51) Int. Cl.[7] .................... A61K 31/437; C07D 471/04
(52) U.S. Cl. .................... 514/292; 546/87; 546/86; 546/80; 546/89; 514/291
(58) Field of Search ................. 514/292, 291; 546/87, 86, 89, 80

(56) References Cited

U.S. PATENT DOCUMENTS

| | | | | |
|---|---|---|---|---|
| 5,162,336 A | * | 11/1992 | Molino et al. | ............ 514/292 |
| 5,936,089 A | | 8/1999 | Carpino et al. | |

FOREIGN PATENT DOCUMENTS

| | | |
|---|---|---|
| WO | WO 98/44921 | 10/1998 |
| WO | WO 98/44922 | 10/1998 |
| WO | WO 98/45285 | 10/1998 |
| WO | WO 99/22735 | 5/1999 |
| WO | WO 99/64401 | 12/1999 |
| WO | WO 99/64420 | 12/1999 |

OTHER PUBLICATIONS

Sadaf Farooqu et al., "The Therapeutic Value of Somastatin and Its Analogues" *Pituitary* vol. 2, pp. 79–88 (1999).

Susan P. Rohrer, et al., "Rapid Identification of Subtype-Selective Agonists of the Somatostatin Receptor Through Combinatorial Chemistry" *Science* vol. 282, pp. 737–740; (1998).

Henning Grønbæk, et al. "Potential Role of Octreotide in the Treatment of Diabetes" *Prog Basic Clin Pharmacol. Basel*, vol. 10, pp. 103–128; (1996).

Vicente Martinez, et al., "High Basal Gastric Acid Secretions in Somatostatin Receptor Subtype 2 Knockout Mice"; American *Gastroenterology* (1998) 114 pp. 1125–1132.

Yogesh C. Patel, et al., "Somatostatin Receptors", *TEM*, vol. 8, No. 10, (1997) pp. 398–404.

Lihu Yang, et al., "Synthesis and biological activities of potent peptidomimetics selective for somastostatin receptor subtype 2"; *Proc. Natl. Acad. Sci. USA*, vol. 95, pp. 10836–10841, (1998).

Simon J. Hocart, et al., "Potent Antagonists of Somatostatin: Synthesis and Biology"; *J. Med. Chem.* vol. 41, pp. 1146–1154.

Muhammad Zaki, et al., "Somatostatin Receptor Subtype 2 Mediates Inhibition of Gastrin and Histamine Secretion from Human, Dog and Rat Antrum"; *Gastroenterology* vol. 111, pp. 919–924 (1996).

William R. Baumbach, et al., "A Linear Hexpeptide Somatostatin Antagonist Blocks Somatostatin Activity In Vitro and Influences Growth Hormone Release in Rats" *Molecular Pharmacology*, vol. 54, pp. 864–873 (1998).

Lihu Yang, et al., "Spiro[1H–indene–1,4–piperidine]Derivatives as Potent and Selective Non–Peptide Human Somatostatin Receptor Subtype 2 (SST2) Agonists", *Journal of Medicinal Chemistry*, vol. 41, No. 13, pp. 2175–2179 (1998).

* cited by examiner

*Primary Examiner*—Charanjit S. Aulakh
(74) *Attorney, Agent, or Firm*—Peter C. Richardson; Gregg C. Benson; Martha G. Munchhof

(57) ABSTRACT

Compounds according to the formula A—Z—W as herein described, wherein A is selected from the groups consisting of: A'—$(CH_2)_n$—, A'—$(CH_2)_nSO_2$—, and A'—$(CH_2)_n$CO—, where n is 0 to 4; and A' is selected from (a) $(C_6-C_{10})$aryl-, or
(b) $(C_1-C_9)$heteroaryl-; which groups may be optionally substituted; and pharmaceutically acceptable salts, solvates or hydrates thereof; pharmaceutical compositions thereof; and methods useful to facilitate secretion of growth hormone(GH) in mammals.

24 Claims, No Drawings

SOMATOSTATIN ANTAGONISTS AND AGONISTS THAT ACT AT THE SST SUBTYPE 2 RECEPTOR

The present application claims priority under 35 USC section 119(e) to U.S. Provisional Application No. 60/249,514, filed Nov. 17, 2000, which is incorporated by reference herein as if fully set forth.

FIELD OF THE INVENTION

The present invention provides pharmaceutically active compounds that facilitate secretion of growth hormone (GH) by the anterior pituitary. Growth hormone (also known as somatotropin) acts indirectly to promote skeletal growth in children by stimulating the production of insulin like growth factor-1 from the liver. Growth hormone also stimulates the differentiation of fat cells and chondrocytes (cells that secrete collagen and proteoglycans to form cartilage). In adults, growth hormone is involved in the proper maintenance of connective and muscle tissues.

Growth hormone deficiency may be congenital or acquired. Deficiency in children causes slow skeletal growth that, if not corrected, results in permanent short stature. In older adults, deficiency of growth hormone results in frailty. Additional adult symptoms of GH deficiency may include wrinkled skin and hypoglycemia.

For veterinary application, upregulation of growth hormone is useful to treat frailty in older animals, particularly companion animals. With respect to livestock, upregulation of growth hormone increases growth and performance, even in healthy animals with normal GH levels. Improvements in feed efficiency, milk yield, leanness, meat quality and fertility are of note.

Although direct administration of growth hormone may be effective in certain therapeutic applications, it is difficult in practice. Among other issues, since the half-life of growth hormone in the body is very short, direct administration leads to artificially increased levels in the concentration of circulating GH, which then rapidly drop off. Sustained release, such as by a mechanical pump, has not been optimally set to practice.

The concentration of growth hormone circulating in the body depends on the balance of numerous biochemical pathways, including opposing processes. Compared to the direct administration approach, shifting the balance of these pathways indirectly provides a safer, more reproducible method to affect GH secretion on a sustained basis. Under this approach, since the overall regulatory framework remains intact, secretion rates and circulatory concentrations for GH follow a relatively normal pattern, and adverse fluctuations in both secretion rate and circulating GH concentration are avoided. The present invention provides for therapeutic compounds, and their use, to indirectly elevate growth hormone secretion from the pituitary.

REPORTED DEVELOPMENTS

Growth hormone is released from the anterior pituitary in response to stimulation by growth hormone releasing peptide (GHRP), and growth hormone releasing hormone (GHRH), of hypothalamic origin. However, release of growth hormone via these or other mechanisms is inhibited by somatostatin, and thus the process is closely regulated.

Somatostatin (SRIF) is a cyclic peptide hormone of 14 amino acids (there is also a 28 amino acid form) having numerous endocrine functions which, like many hormones, is cleaved from a larger precursor protein. Somatostatin inhibits the pituitary secretion of growth hormone, the pancreatic secretion of glucagon and insulin, and the secretion of gastrin from the gut. Somatostatin also acts as a neurotransmitter/neuromodulator (see S. J. Hocart et al., *J. Med. Chem.*,41, pp. 1146–1154, 1998 for a general discussion).

The biological effects of somatostatin are apparently all inhibitory in nature, and are elicited upon binding to the surface of a target cell. The receptor is an integral membrane protein (which spans the cell membrane), and is G-protein-coupled. G-protein coupled receptors represent a major class of cell surface receptors. It is believed that upon binding of somatostatin to the receptor, the receptor undergoes a conformational change facilitating its interaction with a G-protein at the cytoplasmic face of the receptor. This facilitates binding or release of GTP/GDP at the G protein, and leads to further activation and signaling events inside the cell. In particular, somatostatin binding at its own G-protein-coupled receptor is negatively coupled to adenylyl cyclase activity, which is necessary for the production of cyclic AMP. Thus, these further signaling events directly oppose mechanisms (for example, as mediated by calcium ions or cyclic AMP) whereby GHRP and GHRH would otherwise trigger extracellular secretion of growth hormone from cytoplasmic storage granules. For a general review thereof, see *The Encyclopedia of Molecular Biology*, J. Kendrew, ed., Blackwell Science, Ltd. 1994, at page 387.

The effects of somatostatin on target cells are mediated by at least 5 classes of receptors (sst1–sst5). Although the receptors may have similar affinity for somatostatin, they are differentially expressed in different tissues, and so positioned, interact, directly or indirectly, with different intracellular signaling components. This tissue specificity of receptor expression accounts in large measure for the different effects of somatostatin in different target cell types. Somatostatin receptors are found, for example, in tissues of the anterior pituitary, other brain tissues, the pancreas, the lung, on lymphocytes, and on mucosa cells of the intestinal tract.

The sst2 type receptor is known to mediate inhibition of growth hormone secretion in the anterior pituitary. This receptor is also reported in 2 forms, proteins sst2A and sst2B, which result from differential splicing of the sst2 gene transcript (M. Vanetti, et al., FEBS Letters, 311, pp.290–294, 1992). The sst2 receptor is also known to mediate inhibition of gastrin and histamine secretion. Additionally, the sst2 receptor is known to mediate inhibition of glucagon release from pancreatic alpha cells.

Although numerous somatostatin agonists have been described (see for example, WO 98/44922, WO 98/45285, and WO 98/44921), the development of useful sst2-linked somatostatin antagonists has lagged behind. Recent reports of such compounds include W. R. Baumbach et al., *Molecular Pharmacology*, 54, pp. 864–873, 1998, and S. J. Hocart et al., *J. Med. Chem.*, 41, pp. 1146–1154, 1998. However, such compounds are short peptides, a class of molecules not often suited for successful use as pharmaceuticals because of their typically short half life in the body. Additional relevant disclosures include WO099/64401 and WO099/64420.

It would be advantageous to provide antagonists of somatostatin activity, effective at the sst2 type receptor, having superior properties as pharmaceuticals, including bioavailability, stability, and the like. The present invention provides a series of antagonist compounds that specifically interfere with the binding of somatostatin to the sst subtype 2 receptors of cells in the mammalian anterior pituitary, and which have additional valuable properties.

SUMMARY OF THE INVENTION

Accordingly, there are provided compounds according to the formula

A—Z—W  (formula I)

or pharmaceutically acceptable salts, solvates or hydrates thereof; wherein A is selected from the groups consisting of:
A'—$(CH_2)_n$—, A'—$(CH_2)_n SO_2$—, and A'—$(CH_2)_n CO$—,
where n is 0 to 4; and
A' is selected from
(a) $(C_6-C_{10})$aryl-, selected from phenyl or naphthyl; or
(b) $(C_1-C_9)$heteroaryl-, selected from the group consisting of furyl-, thienyl-thiazolyl-, pyrazolyl-, isothiazolyl-, oxazolyl-, isoxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5,6,7,8-tetrahydro-quinolin-3-yl, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl- quinolyl-, phthalazinyl-, quinoxalinyl-, quinazolinyl-, and benzoxazinyl-;
wherein said A' group (a) or (b) is optionally substituted by zero to seven, preferably zero to five groups, each independently selected from:
hydroxy, halo, amino, trifluoromethyl-, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano, nitro, $(C_1-C_6)$alkyl-, $(C_2-C6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$alkyl(difluoromethylene)$(C_1-C_3)$alkyl-, $(C_1-C_6)$acylamino$(C_1-C_6)$alkyl-, $(C_1-C_6)$alkoxy$(C_1-C_6)$acylamino-, amino$(C_1-C_6)$acyl-, amino$(C_1-C_6)$acyl$(C_1-C_6)$alkyl-, $(C_1-C_6)$alkylamino$(C_1-C_6)$acyl-, $((C_1-C_6)$alkyl$)_2$amino$(C_1-C_6)$acyl-, $(C_3-C_{10})$cycloalkyl$(C_1-C_6)$alkyl-, $(C_2-C_6)$alkoxy$(C_1-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_1-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, $(C_1-C_6)$alkyl(difluoromethylene)—, $(C_1-C_3)$alkyl(difluoromethylene)$(C_1-C_3)$alkyl-, $(C_1-C_6)$alkoxy$(C_1-C_6)$acyl-, $(C_1-C_6)$alkylamino$(C_1-C_6)$acyl-, $((C_1-C_6)$alkyl$)_2$ amino$(C_1-C_6)$acyl-, $(C_6-C_{10})$aryl-, $(C_1-C_9)$heteroaryl-, $(C_6-C_{10})$aryl$(C_1-C_6)$alkyl-, $(C_1-C_9)$heteroaryl$(C_1-C_6)$alkyl-, $(C_6-C_{10})$aryl$(C_6-C_{10})$aryl-, $(C_6-C_{10})$aryl$(C_6-C_{10})$alkyl-$(C_3-C_{10})$cycloalkyl-, $(C_3-C_6)$cycloalkyl$(C_1-C_6)$alkyl-, $(C_3-C_{10})$heterocycloalkyl-, $(C_3-C_{10})$heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_1-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$alkylsulfonyl$(C_1-C_6)$alkyl-$(C_6-C_{10})$ arylsulfonyl$(C_1-C_6)$alkyl-, amino$(C_1-C_6)$alkyl-, $(C_1-C_6)$alkylamino$(C_1-C_6)$alkyl-, and $((C_1-C_6)$alkyl$)_2$amino$(C_1-C_6)$alkyl-;
Z is selected from groups (i) to (iv):

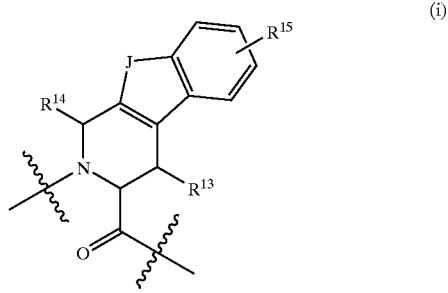

(i)

where $R^{13}$ is H, or $(C_1-C_6)$alkyl optionally substituted by one or more halo groups;
$R^{14}$ is H, $(C_1-C_6)$alkyl, trifluoro$(C_1-C_6)$alkyl-, or phenyl $(CH_2)$—, wherein said alkyl and phenyl groups are each optionally substituted by one or more halo groups, or $R^{14}$ is selected from the groups A above, optionally substituted by one or more halo groups;
$R^{15}$ is selected from hydroxy, halo, $(C_1-C_6)$alkyl- optionally substituted by one or more halo, and $(C_1-C_6)$alkoxy- optionally substituted by one or more halo; and
J is S, O, —NH—, or $NCH_3$;

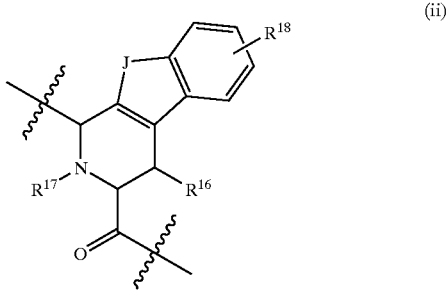

(ii)

where $R^{16}$ is H, or $(C_1-C_6)$alkyl optionally substituted by one or more halo groups;
$R^{17}$ is a group selected from $R^{14}$ above, or $R^{14}K$—where K is —C(O)— or —$SO_2$—; and
$R^{18}$ is selected from hydroxy, halo, $(C_1-C_6)$alkyl- optionally substituted by one or more halo, and $(C_1-C_8)$alkoxy-optionally substituted by one or more halo; and
J is S, O, —NH—, or $NCH_3$;

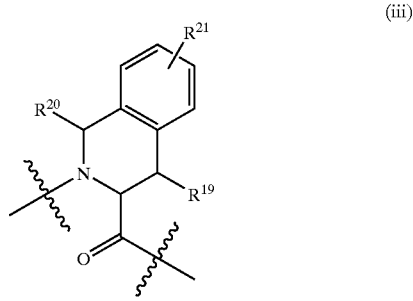

(iii)

where $R^{19}$ is H, or $(C_1-C_6)$alkyl optionally substituted by one or more halo groups;
$R^{20}$ is H, $(C_1-C_6)$alkyl, trifluoro$(C_1-C6)$alkyl-; or phenyl $(CH_2)$—, wherein said alkyl and phenyl groups are each optionally substituted by one or more halo groups, or $R^{20}$ is selected from the groups A above, optionally substituted by one or more halo groups; and $R^{21}$ is selected from hydroxy, halo, $(C_1-C_6)$alkyl- optionally substituted by one or more halo, and $(C_1-C_8)$alkoxy- optionally substituted by one or more halo; and

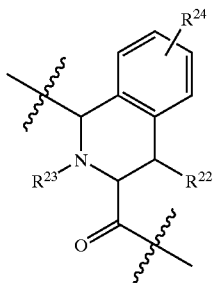

(iv)

where $R^{22}$ is H, or $(C_1-C_6)$alkyl optionally substituted by one or more halo groups;

$R^{23}$ is a group selected from $R^{14}$ above, or is $R^{14}K-$ where K is $-C(O)-$ or $-SO_2-$; and $R^{24}$ is selected from hydroxy, halo, $(C_1-C_6)$alkyl- optionally substituted by one or more halo, and $(C_1-C_8)$alkoxy- optionally substituted by one or more halo;

W is (a):

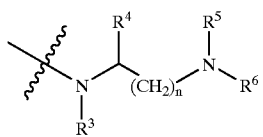

(a)

wherein n is 2–5, $R^3$ and $R^6$ are each independently selected from H, $(C_1-C_8)$alkyl-, and phenyl$(CH_2)-$, wherein said alkyl and phenyl groups are optionally substituted by one or more halo groups;

$R^4$ is selected from H, $(C_1-C_8)$alkyl-, and phenyl$(CH_2)-$, wherein said alkyl and phenyl groups are optionally substituted by one or more halo groups; or is

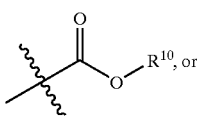

(1)

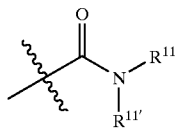

(2)

where groups $R^{10}$, $R^{11}$ and $R^{11'}$ are each, independently, selected from H, $(C_1-C_8)$alkyl-, and phenyl$(CH_2)-$, wherein said alkyl and phenyl groups are optionally substituted by one or more halo groups;

$R^5$ is H, $(C_1-C_8)$alkyl-, and phenyl$(CH_2)-$, wherein said alkyl and phenyl groups are optionally substituted by one or more halo groups; or is

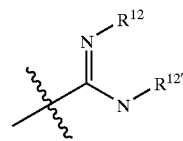

wherein $R^{12}$ and $R^{12'}$ are each independently selected from H, $(C_1-C_8)$alkyl-, and phenyl$(CH_2)-$, wherein said alkyl and phenyl groups are optionally substituted by one or more halo groups;

or W is (b)

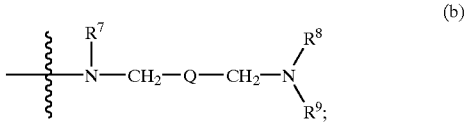

(b)

wherein Q is selected from the group consisting of:
(i) $(C_6-C_{10})$aryl-, selected from phenyl or naphthyl;
(ii) $(C_1-C_9)$heteroaryl-, selected from the group consisting of furyl-, thienyl- thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H[1]pyrindinyl-, benzo[b]thiophenyl-, 5,6,7,8-tetrahydro-quinolin-3-yl, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl- quinolyl-, phthalazinyl-, quinoxalinyl-, quinazolinyl-, and benzoxazinyl-;
(iii) $(C_3-C_{10})$cycloalkyl that is selected from the group consisting of cyclopropyl-, cyclobutyl-, cyclopentyl-; cyclohexyl-, cycloheptyl-, cyclopropenyl-, cyclobutenyl-, cyclohexenyl-, cycloheptenyl-, 1,3-cyclobutadienyl-, 1,3-cyclopentadienyl-, 1,3-cyclohexadienyl-, 1,4-cyclohexadienyl-1,3-cycloheptadienyl-, 1,4-cycloheptadienyl-, 1,3,5-cycloheptatrienyl- bicyclo[3.2.1]octane, bicyclo[2.2.1]heptane and the norborn-2-ene unsaturated form thereof; and
(iv) $(C_3-C_{10})$heterocycloalkyl that is selected from the group consisting of pyrrolidinyl-, tetrahydrofuranyl- dihydrofuranyl-, tetrahydropyranyl-, pyranyl-, thiopyranyl-, aziridinyl-, oxiranyl-, methylenedioxyl-, chromenyl-, isoxazolidinyl-, 1,3-oxazolidin-3-yl- isothiazolidinyl-, 1,3-thiazolidin-3-thiazolidin-3-yl-, 1,2-pyrazolidin-2-yl-, 1,3-pyrazolidin-1-yl-, piperidinyl-, thiomorpholinyl-, 1,2-tetrahydrothiazin-2-yl-, 1,3-tetrahydrothiazin-3-yl-, tetrahydrothiadiazinyl-, morpholinyl-, 1,2-tetrahydrodiazin-2-yl-, 1,3-tetrahydrodiazin-1-yl-, tetrahydroazepinyl-, piperazinyl-, and chromanyl;

and $R^7$, $R^8$, and $R^9$ are each independently selected from H, $(C_1-C_8)$alkyl-, and phenyl$(CH_2)-$, wherein said alkyl and phenyl groups are optionally substituted by one or more halo groups.

In a preferred embodiment of the invention, where one or more of $R^{13}$, $R^{16}$, $R^{19}$ and $R^{22}$ is halo$(C_1-C_6)$alkyl-, the preferred halo species is fluoro, wherein trifluoromethyl- is most preferred.

Preferred compounds of the invention include:

6-Amino-2-{[2-(toluene-4-sulfonyl)-2,3,4,9-tetrahydro-1Hβ-carboline-3-carbonyl]-amino}-hexanoic acid methyl ester;

6-Amino-2-{[2-(biphenyl-4-sulfonyl)-2,3,4,9-tetrahydro-1H-β-carboline-3-carbonyl]-amino}-hexanoic acid methyl ester;

6-Amino-2-{[2-biphenyl-4-carbonyl)-2,3,4,9-tetrahydro-1H-β-carboline-3-carbonyl]-amino}-hexanoic acid methyl ester;

6-Amino-2-[(2-biphenyl-4-ylmethyl-2,3,4,9-tetrahydro-1H-β-carboline-3-carbonyl)-amino]-hexanoic acid methyl ester;

6-Amino-2-{[1-(3-benzyloxy-phenyl)-2,3,4,9-tetrahydro-1Hβ-carboline-3-carbonyl]-amino}-hexanoic acid methyl ester;

6-Amino-2-({1-[4(4-trifluoromethyl-phenoxy)-phenyl]-2,3,4,9-tetrahydro-1H-β-carboline-3-carbonyl}-amino)-hexanoic acid methyl ester;

6-Amino-2-{[1-(4-butyl-phenyl)-2,3,4,9-tetrahydro-1H-β-carboline-3-carbonyl]-amino}-hexanoic acid methyl ester;

6-Amino-2-{[1-(4-pyrrolidin-1-yl-phenyl)-2,3,4,9-tetrahydro-1H-β-carbonyl-3-carbonyl]-amino}-hexanoic acid methyl ester;

6-Amino-2-({1[2-(4-isopropyl-phenyl)-1-methyl-ethyl]-2,3,4,9-tetrahydro-1H-β-carboline-3-carbonyl}-amino)-hexanoic acid methyl ester;

6-Amino-2-({1-[3-(4-trifluoromethyl-phenoxy)-phenyl]-2,3,4,9-tetrahydro-1H-βcarboline-3-carbonyl}-amino)-hexanoic acid methyl ester;

6-Amino-2{[1-(3-benzyloxy-phenyl)-2,3,4,9-tetrahydro-1H-β-carboline-3-carbonyl]-amino}-hexanoic acid methyl ester;

6-Amino-2-{[1-(3-benzyloxy-phenyl)-2,3,4,9-tetrahydro-1H-β-carboline-3-carbonyl]-amino}-hexanoic acid methyl ester;

6-Amino-2-{[1-(1-methyl-3-phenyl-butyl)-2,3,4,9-tetrahydro-1H-β-carboline-3-carbonyl]-amino}-hexanoic acid methyl ester;

6-Amino-2-{[2-(toluene-4-sulfonyl)-2,3,4,9-tetrahydro-1H-β-carboline-3carbonyl]-amino}-hexanoic acid tert-butyl ester;

5-Guanidino-2-{[2-(toluene-4-sulfonyl)-1,2,3,4-tetrahydro-isoquinoline-3-carbonyl]-amino}-pentanoic acid tert-butyl ester;

5-Guanidino-2-{[2-(toluene-4-sulfonyl)-1,2,3,4-tetrahydro-isoquinoline-3-carbonyl]-amino}-pentanoic acid methyl ester;

6-Amino-2-({2-[4-(2-oxo-2,3-dihydro-benzoimidazol-1-y)-piperidine-1-carbonyl]-2,3,4,9-tetrahydro-1H-β-carboline-3-carbonyl}-amino)-hexanoic acid tert-butyl ester;

6-Amino-2-({2-[(1H-indol-3-yl)-acetyl]-tetrahydro-1H-β-carboline-3-carbonyl}-amino)-hexanoic acid methyl ester;

6-Amino-2-{[1-(4-isopropyl-phenyl)-2,3,4,9-tetrahydro-1H-β-carboline-3-carbonyl]-amino}-hexanoic acid methyl ester; and 6-Amino-2-{[1-(3-trifluoromethyl-phenyl)-2,3,4,9-tetrahydro-1H-β-carboline-3-carbonyl]-amino}-hexanoic acid methyl ester.

Additional compounds of the invention include:

6-Amino-2-{[4-methyl-2-(toluene-4-sulfonyl)-2,3,4,9-tetrahydro-1H-β-carboline-3-carbonyl]-amino}-hexanoic acid methyl ester;

6-Amino-2-{[4-methyl-2-(toluene-4-sulfonyl)-2,3,4,9-tetrahydro-1H-β-carboline-3-carbonyl]-amino}-hexanoic acid tert-butyl ester;

6-Amino-2-{[2-(biphenyl-4-sulfonyl)-2,3,4,9-tetrahydro-1H-β-carboline-3-carbonyl]-amino}-hexanoic acid tert-butyl ester;

6-Amino-2-{[2-(biphenyl-4-carbonyl)-2,3,4,9-tetrahydro-1H-β-carboline-3-carbonyl]-amino}-hexanoic acid tert-butyl ester;

6-Amino-2-[(2-biphenyl-4-ylmethyl-2,3,4,9-tetrahydro-1H-β-carboline-3-carbonyl)-amino]-hexanoic acid ter-butyl ester;

2-(Toluene-4-sulfonyl)-2,3,4,9-tetrahydro-1H-β-carboline-3-carboxylic acid (3-aminomethyl-cyclohexylmethyl)-amide;

2-(Toluene-4-sulfonyl)-2,3,4,9-tetrahydro-1H-β-carboline-3-carboxylic acid (4-aminomethyl-pyridin-2-ylmethyl-amide;

2-(Biphenyl-4-sulfonyl)-2,3,4,9-tetrahydro-1H-β-carboline-3-carboxylic acid (3-aminomethyl-cyclohexylmethyl)-amide;

2-(Biphenyl-4-sulfonyl)-2,3,4,9-tetrahydro-1H-β-carboline-3-carboxylic acid (4-aminomethyl-pyridin-2-ylmethyl)-amide;

2-(Biphenyl-4-carbonyl)-2,3,4,9-tetrahydro-1H-β-carboline-3-carboxylic acid (3-aminomethyl-cyclohexylmethyl)-amide;

2-(Biphenyl-4-carbonyl)-2,3,4,9-tetrahydro-1H-β-carboline-3-carboxylic acid (4-aminomethyl-pyridin-2-ylmethyl)-amide;

2-(Biphenyl-4-ylmethyl-2,3,4,9-tetrahydro-1H-β-carboline-3-carboxylic acid (3-aminomethyl-cyclohexylmethyl)-amide;

2-Biphenyl-4-ylmethyl-2,3,4,9-tetrahydro-1H-β-carboline-3-carboxylic acid (4-aminomethyl-pyridin-2-ylmethyl)-amide;

6-Amino-2-{[1-(3-benzyloxy-phenyl)-2,3,4,9-tetrahydro-1H-β-carboline-3-carbonyl]-amino}-hexanoic acid tert-butyl ester;

1-(3-Benzyloxy-phenyl)-2,3,4,9-tetrahydro-1Hβ-carboline-3-carboxylic acid (3-aminomethyl-cyclohexylmethyl)-amide;

1-(3-Benzyloxy-phenyl)-2,3,4,9-tetrahydro-1H-β-carboline-3-carboxylic acid (4-aminomethyl-pyridin-2-ylmethyl)-amide;

1-[4-(4-Trifluoromethyl-phenoxy)-phenyl]-2,3,4,9-tetrahydro-1H-β-carboline-3-carboxylic acid (3-aminomethyl-cyclohexylmethyl)-amide;

1-[4-(4-Trifluoromethyl-phenoxy)-phenyl]-2,3,4,9-tetrahydro-1H-β-carboline-3-carboxylic acid (4-aminomethyl-pyridin-2-ylmethyl)-amide;

6-Amino-2-({1-[4-(4-trifluoromethyl-phenoxy)-phenyl]-2,3,4,9-tetrahydro-1H-β-carboline-3-carbonyl}-amino)-hexanoic acid tert-butyl ester;

6-Amino-2-{[2-(4-methyl-benzoyl)-2,3,4,9-tetrahydro-1H-β-carboline-3-carbonyl]-amino}-hexanoic acid tert-butyl ester;

6-Amino-2-{[2-(4-methyl-benzyl)2,3,4,9-tetrahydro-1H-β-carboline-3-carbonyl]-amino}-hexanoic acid tert-butyl ester;

6-Amino-2-[(2-benzyl-2,3,4,9-tetrahydro-1H-β-carboline-3-carbonyl)-amino]-hexanoic acid tert-butyl ester;

6-Amino-2-[(2-benzoyl-2,3,4,9-tetrahydro-1H-β-carboline-3-carbonyl)-amino]-hexanoic acid tert-butyl ester;

6-Amino-2-[2-benzenesulfonyl-2,3,4,9-tetrahydro-1H-β-carboline-3-carbonyl)-amino]-hexanoic acid tert-butyl ester;

6-Amino-2-{[1-methyl-2-(toluene-4-sulfonyl)-2,3,4,9-tetrahydro-1H-β-carboline-3-carbonyl]-amino}-hexanoic acid tert-butyl ester;

6-Amino-2-{[1-(3-benzyloxy-phenyl)-1-methyl-2,3,4,9-tetrahydro-1H-β-carboline-3-carbonyl]-amino}-hexanoic acid tert-butyl ester;

6-Amino-2-({1-[3-(4-fluoro-benzyloxy)-phenyl]-2,3,4,9-tetrahydro-1H-β-carboline-3-carbonyl}-amino)-hexanoic acid tert-butyl ester;

6-Amino-2-{[1-(2-benzyloxy-pyridin-4-yl)-2,3,4,9-tetrahydro-1H-β-carboline-3-carbonyl]-amino}-hexanoic acid tert-butyl ester;

6-Amino-2-({1-[3-(pyridin-2-ylmethoxy)-phenyl]-2,3,4,9-tetrahydro-1H-β-carboline-3-carbonyl}-amino)-hexanoic acid tert-butyl ester;

6-Amino-2-({1-[3-(1-phenyl-ethoxy)-phenyl]-2,3,4,9-tetrahydro-1H-β-carboline-3-carbonyl}-amino)-hexanoic acid tert-butyl ester;

6-Amino-2-{[1-(4-phenoxy-phenyl)-2,3,4,9-tetrahydro-1H-β-carboline-3-carbonyl]-amino}-hexanoic acid methyl ester;

2-[(2-Benzoyl-1,2,3,4-tetrahydro-isoquinoline-3-carbonyl)-amino]-5-guanidino-pentanoic acid tert-butyl ester;

2-[(2-Benzyl-1,2,3,4-tetrahydro-isoquinoline-3-carbonyl)-amino]-5-guanidino-pentanoic acid tert-butyl ester; and 2-[(2-Benzenesulfonyl-1,2,3,4-tetrahydro-isoquinoline-3-carbonyl)-amino]-5-guanidino-pentanoic acid tert-butyl ester.

The compounds and pharmaceutical compositions of this invention include all conformational isomers of compounds of formula I (eq., cis and trans isomers, whether or not involving double bonds). The compounds of the invention include all optical isomers of the compounds of formula I (e.g., enantiomers and diastereomers), as well as racemic, diastereomeric and other mixtures of all such isomers. This invention further relates to tautomers and stereoisomers of the compounds of formula (I), and mixtures of any of the aforementioned forms. As will be described below in greater detail, certain isomeric structures are preferred.

The present invention also relates to the pharmaceutically acceptable acid addition salts of compounds of the formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

With respect to the relatively limited number of compounds that so permit, the invention also relates to base addition salts of formula (I). The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (eq., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon 14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula (I) of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for increasing growth hormone secretion in a mammal, including a human, comprising an effective amount of a compound according to formula 1, and a pharmaceutical carrier. The present invention also relates to a pharmaceutical composition for increasing gastrin secretion or glucagon secretion in a mammal, comprising an effective amount of a compound according to formula 1, and a pharmaceutical carrier.

The present invention also relates to a pharmaceutical composition for the treatment of diseases characterized by decreased levels of growth hormone, glucagon, or gastrin in a mammal, including a human, comprising an amount of a compound of formula (I) effective in such treatments and a pharmaceutically acceptable carrier. The present invention also relates to a pharmaceutical composition for the treatment of diseases in a mammal, including a human, wherein treatment can be effected by inhibiting the binding of somatostatin to the sst2-type receptor therefor, comprising an effective amount of a compound according to formula 1, and a pharmaceutical carrier.

The present invention relates to a method for treating growth hormone deficiency in a mammal, including a human. The present invention also relates to elevating the level of growth hormone in a mammal, including a human, wherein this is beneficial to the mammal nothwithstanding that the natural levels of growth hormone present in the mammal are within the normal range. In the practice of said method, there is administered a pharmaceutical composition of the invention comprising a compound according to formula (1), and a pharmceutical carrier.

Similarly, the methods of the invention provide for increasing gastrin secretion or glucagon secretion in a mammmal, including a human, where this is medically appropriate. For example, gastrin is involved in protection of gastric mucosa against damage by chemical substances, e.g. alcohol (S. J. Konturek et al., *European Journal of Pharmacology*, 278(3), pp. 203–212, 1995). Glucagon is a counter-regulatory hormone that is used to treat hypoglycemia, and causes positive inotropic and chronotropic effects without the need for beta-1adrenoceptor stimulation. It also can be used to correct beta-blocker, verapamil and imipramine overdose, and is used as adjunctive therapy in shock situations, for heart failure, and in treating post-countershock asystole (see C. M. White, *Journal of Clinical Pharmacology*, 39(5), pp. 442–447, 1999)

In preferred examples of the invention, there are provided methods for treating a human for one or more symptoms of insufficient growth hormone secretion, or one or more conditions that may occur therewith and be exacerbated thereby, wherein said condition is selected from frailty, hypoglycemia, wrinkled skin, slow skeletal growth, reduced immune function, reduced organ function, fertility disorders, bone disease, AIDS-related complex, cachexia, cardiac failure, ischemic heart disease, colon disease, metabolic disorders, renal failure, muscular dystrophy, and Turners syndrome, comprising administering an effective amount of a pharmaceutical composition as aforementioned. It will be appreciated that numerous of the above conditions also affect non-human mammals, and treatment of such conditions is also within the practice of the invention.

In a further preferred example of the invention, there is provided a method for treating a non-human mammal to enhance the growth and performance thereof, comprising administering an effective amount of a pharmaceutical composition as aforementioned. Enhancement of growth and performance includes, for example, increased feed efficiency, improved milk yield or fertility, and increased leanness.

A highly preferred example of the invention provides a method wherein by secretion of growth hormone, gastrin, or glucagon can be increased on a sustained basis in a mammal, including a human, in need thereof, comprising administering a dose of a pharmaceutical composition as aforementioned. According to this example of the invention, physiologically adverse consequences of artificial fluctuations in the circulating (or locally needed) concentrations of these hormones can be avoided.

Although the pharmaceutical compositions and methods of the invention are described primarily in terms of use with humans, and non-human mammals, the skilled practitioner will immediately appreciate that the invention, in many of its aspects, may be usefully practiced with respect to birds, such as chickens and turkeys, and also fishes.

DEFINITIONS

In connection with the practice of the invention, the following definitions will generally apply.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "alkyl", as used herein, unless otherwise indicated, includes saturated monovalent hydrocarbon radicals having straight, branched or cyclic moieties or combinations thereof. Similarly, the terms "alkenyl" and "alkenyl" define hydrocarbon radicals having straight, branched or cyclic moities wherein at least one double bond, or at least one triple bond, respectively, is present. Such definitions also apply when the alkyl, alkenyl or alkynyl group is present within another group, such as alkoxy or alkylamine.

The term "alkoxy", as used herein, includes O-alkyl groups wherein "alkyl" is as defined above.

The term "halo", as used herein, unless otherwise indicated, includes fluoro, chloro, bromo or iodo.

An "aryl" group as used herein, unless otherwise indicated, includes an organic radical derived from a monocyclic or bicylic ($C_6$–$C_{10}$) aromatic hydrocarbon compound by removal of a hydrogen radical from a ring carbon of the aryl compound. An aryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative aryl groups are phenyl and naphthyl.

A "heteroaryl" group as used herein, unless otherwise indicated, includes an organic radical derived from a monocyclic or bicyclic ($C_1$–$C_9$) aromatic heterocyclic compound by removal of a hydrogen radical from a ring atom of the heteroaryl compound, said ring atom being uncharged in said compound. A heteroaryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heteroaryl groups include furyl-, thienyl-, thiazolyl- pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl-, pyrimidyl-, pyrazinyl-, pyridazinyl-, 1,2,4-triazinyl- 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5,6,7,8-tetrahydro-quinolin-3-yl-, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl-, quinolyl-, phthalazinyl-, quinoxalinyl-, quinazolinyl-, benzoxazinyl-; and the like.

A "cycloalkyl" group as used herein, unless otherwise indicated, includes an organic radical derived from a monocyclic ($C_3$–$C_{10}$)cycloalkyl compound, by removal of a hydrogen radical from a ring carbon of the cycloalkyl compound. A cycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative cycloalkyl groups include cyclopropyl, cyclobutyl, cyclopentyl, cyclohexyl, cycloheptyl, cyclopropenyl, cyclobutenyl, , cyclohexenyl, cycloheptenyl, 1,3-cyclobutadienyl, 1,3-cyclopentadienyl, 1,3-cyclohexadienyl, 1,4-cyclohexadienyl, 1,3-cycloheptadienyl, 1,4-cycloheptadienyl, 1,3,5-cycloheptatrienyl, bicyclo[3.2.1] octane, bicyclo [2.2.1] heptane, and the norborn-2-ene unsaturated form thereof. Thus, the term cycloalkyl also includes cycloalkenyl groups having one or two double bonds.

A "heterocycloalkyl" group as used herein, unless otherwise indicated, includes an organic radical derived from a monocyclic ($C_3$–$C_{10}$)heterocycloalkyl compound by removal of a hydrogen radical from a ring atom of the heterocycloalkyl compound. A heterocycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heterocycloalkyl groups include pyrrolidinyl-, tetrahydrofuranyl-, dihydrofuranyl-, tetrahydropyranyl-, pyranyl-, thiopyranyl-, aziridinyl-, oxiranyl-, methylenedioxyl-, chromenyl-, isoxazolidinyl-, 1,3-oxazolidin-3-yl-, isothiazolidinyl-, 1,3-thiazolidin-3-yl, 1,2-pyrazolidin-2-yl, 1,3-pyrazolidin-1-yl, piperidinyl-, thiomorpholinyl-, 1,2-tetrahydrothiazin-2-yl, 1,3-tetrahydrothiazin-3-yl, tetrahydrothiadiazinyl-, morpholinyl-, 1,2-tetrahydrodiazin-2-yl, 1,3-tetrahydrodiazin-1-yl, tetrahydroazepinyl, piperazinyl-, and chromanyl-.

In connection with the terms "aryl" group, "heteroaryl" group, "cycloalkyl" group and "heterocycloalkyl" group, as herein defined, the term "optionally substituted" means that one or more chemically and pharmaceutically acceptable functional groups may be bonded thereto. Such a group contributes properties useful to production, storage, or use of the inventive compounds as pharmaceuticals, or at least does not substantially negate their pharmacological activity. Such suitable substituents may be determined by those skilled in the art. Illustrative examples of suitable substituents include, but are not limited to,. hydroxy, halo, amino, trifluoromethyl, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$ acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_2-C_6)$alkyl-, nitro$(C_1-C_6)$alkyl-, $(C_1-C_3)$ alkyl(difluoromethylene)$(C_1-C_3)$alkyl-, $(C_1-C_6)$acylamino $(C_1-C_6)$alkyl-, $(C_1-C_6)$alkoxy$(C_1-C_6)$acylamino-, amino $(C_1-C_6)$aryl-, amino$(C_1-C_6)$acyl$(C_1-C_6)$alkyl-, $(C_1-C_6)$ alkylamino$(C_1-C_6$acyl-, $((C_1-C_6)$alkyl$)_2$amino$(C_1-C_6)$ acyl-, $(C_3-C_{10})$cycloalkyl$(C_1-C_6)$alkyl-, $(C_1-C_6)$acyloxy $(C_1-C_6)$alkyl-, $(C_2-C_6)$alkoxy$(C_1-C_6)$alkyl-, piperazinyl $(C_1-C_6)$alkyl-, $(C_1-C_6)$acylamino$(C_1-C_6)$alkyl-, $(C_6-C_{10})$ aryl$(C_1-C_6)$alkoxy$(C_1-C_6)$alkyl-, $(C_1-C_9)$heteroaryl $(C_1-C_6)$alkoxy$(C_1-C_6)$alkyl-, $(C_1-C_6)$alkylthio$(C_1-C_6)$ alkyl-, $(C_6-C_{10})$arylthio$(C_1-C_6)$alkyl-, $(C_1-C_6)$alkylsulfinyl $(C_1-C_6)$alkyl-, $(C_6-C_{10})$arylsulfinyl$(C_1-C_6)$alkyl-, $(C_1-C_6)$ alkylsulfonyl$(C_1-C_6)$alkyl-, $(C_6-C_{10})$arylsulfonyl$(C_1-C_6)$ alkyl-, amino$(C_1-C_6)$alkyl-, $(C_1-C_6)$alkylamino$(C_1-C_6)$ alkyl-, $(C_1-C_6)$alkyl(difluoromethylene)—, $(C_1-C_3)$alkyl (difluoromethylene)$(C_1-C_3)$alkyl-, $(C_1-C_6)$alkoxy$(C_1-C_6)$ acyl-, $(C_1-C_6)$alkylamino$(C_1-C_6)$acyl-, $((C_1-C_6)$alkyl$)_2$ amino$(C_1-C_6)$acyl-, $(C_6-C_{10})$aryl-, $(C_1-C_9)$heteroaryl-, $(C_6-C_{10})$aryl$(C_1-C_6)$alkyl-, $(C_1-C_9)$heteroaryl$(C_1-C_6)$ alkyl-, $(C_6-C_{10})$aryl$(C_6-C_{10})$aryl-, $(C_6-C_{10})$aryl$(C_6-C_{10})$ aryl$(C_1-C_6)$alkyl- $(C_3-C_{10})$cycloalkyl-, $(C_3-C_6)$cycloalkyl $(C_1-C_6)$alkyl-, $(C_3-C_{10})$heterocycloalkyl-, $(C_3-C_{10})$ heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxyl$(C_2-C_6)$ alkyl-, piperazinyl$(C_1-C_6)$alkyl-, $(C_1-C_6)$acylamino $(C_1-C_6)$alkyl-, $(C_6-C_{10})$aryl$(C_1-C_6)$alkoxy$(C_1-C_6)$alkyl-, $(C_1-C_9)$heteroaryl$(C_1-C_6)$alkoxy$(C_1-C_6)$alkyl-, $(C_1-C_6)$ alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinyl $(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, and $((C_1C_6)$alkyl$)_2$amino $(C_1-C_6)$alkyl.

Further aspects of the invention are described in accord with the Detailed Description of the invention which follows directly.

DETAILED DESCRIPTION OF THE INVENTION

According to the practice of the present invention, the secretion of growth hormone (GH) from cells (such as those of the anterior pituitary) is facilitated by inhibiting the somatostatin-induced (and G-protein coupled) mechanisms that otherwise naturally act to oppose said secretion. Without being limited as to theory, these somatostatin-induced mechanisms act to oppose both calcium ion and cyclic AMP-mediated signals that otherwise enhance fusion with the cell membrane of cytoplasmic granule structures that contain growth hormone, and thus the subsequent release (secretion) of GH.

The present invention provides an effective approach to the treatment of frailty in older persons, which may be caused, in whole or part, by insufficient levels of growth hormone (GH), or impairment of any of several downstream physiological effects normally associated with growth hormone secretion.

It is generally recognized that GH is important to the maintenance of connective and muscle tissue in adults, and may help, to some extent, to increase muscle mass. Thus growth hormone may be used to assist elderly patients even when growth hormone levels per se are not the cause of, for example, weakness, or attrition of muscle and connective tissues.

The practice of the invention benefits other patients, such as children, when it can be demonstrated that secretion of GH is inadequate, but is subject to enhancement. Deficiency in GH secretion, or resultant GH activity, may arise in several ways. For example, the gene sequence that encodes GH may be expressed in the nucleus at subnormal levels, processing of resultant RNA transcript or nascent polypeptide may be defective, or fusion of cytoplasmic GH storage granules with the cell membrane (with resultant release of GH) may be defective. Additionally, the patient may possess an allele of the GH gene that encodes a mutant protein having less biological activity. Alternatively, there may be an underlying deficiency of GHRH, or a defect in the GHRH receptor, or defects in the GHRP receptor or deficiency of its endogenous ligand, or in respective signaling mechanisms. Additionally, there may be an excess of somatostatin. In all such cases, the resultant physiological deficiency can be treated by administration of the pharmaceutical compounds of the invention.

In a further aspect of the invention, the performance and growth rate of non-human mammals, such as livestock, is enhanced by appropriate administration of the compounds disclosed herein. Additionally, companion animals, and particularly older companion animals also benefit upon administration of the present compounds.

Under appropriate circumstances, somatostatin antagonists may also exhibit the properties of agonists, and are thus recognized as useful therapeutics in the treatment of diabetes, for example, see H. Grønbaeck et al., *Prog. Basic Clin Pharmacol.* (Basel), 10, pp. 103–128, 1996. Somatostatin agonists are also recognized (see WO 98/44922) as useful therapeutics in the treatment of, for example, diabetic retinopathy, acromegaly, rheumatoid arthritis, neuropathic and visceral pain, irritable bowel syndrome, Crohn's disease, and are useful to inhibit cell proliferation associated with cancer, and to prevent restenosis following angioplasty.

Additionally, sst2 ligands can evidence affinity for other G protein-coupled receptors including the melanocortin receptor, the MCH receptor, and MCR4. It is also expected that sst2 ligands will evidence affinity for the MCH receptor SLC1(somatostatin-like receptor 1) since it is more than 50% homologous to sst2. Accordingly, the compounds of the present invention are also useful in the treatment of medical conditions mediated through these receptors including, for example, treatment or prevention of obesity, diabetes mellitus, erectile dysfunction and female sexual dysfunction. Additionally, the compounds of the present invention are useful to modulate appetite and metabolic rate. In particular, the compounds of the present invention are useful to stimulate the appetite of mammals for the treatment of diseases/disorders associated with inappropriate food intake and weight loss, and for example, to enhance growth and survivability of neonates in livestock.

Although the compounds of the present invention act to indirectly facilitate release of mature growth hormone from the cytoplasmic storage granules of cells, additional therapeutic substances are known that can directly enhance such secretion, and further, can indirectly enhance production of growth hormone by via enhanced expression of GH-encoding DNA in the cell nucleus. In this regard, both growth hormone releasing peptide (GHRP) and growth hormone releasing hormone (also known as growth hormone releasing factor, GHRH/GRF) which act to release GH from cytoplasmic storage granules have been mentioned. Since the release of GH from such granules has been implicated as a signal triggering production of additional GH protein in the cells, it is expected that GH levels may be properly maintained in patients using a "push-pull" approach.

Accordingly, a further preferred example of the invention provides for the co-administration of the somatostatin-antagonist compounds of the present invention and GHRP or GHRH, or other substances of like effects. Medical treatment with GHRP (or GHRH) alone is described in the following representative publications: M. Thorner et al., *Journal Of Clinical Endocrinology And Metabolism*, 81(3), pp. 1189–1196, 1996; S. G. Celia et al., Peptides, 16(1), pp. 81–86, 1995; M. A. Bach et al., *Journal Of The American Geriatrics Society*, 44(9), S10, 1996; and J. A. Aloi et al., *Journal Of Clinical Endocrinology And Metabolism*, 79(4), pp. 943–949, 1994.

Further, since growth hormone is very labile, and its half-life in the body is very short, it is difficult to provide a safe dosing program for direct administration of growth hormone itself, which avoids wide swings in circulating levels of the hormone. Current sustained release technologies for direct administration of growth hormone can be improved upon. In this regard, the practice of the present invention is particularly valuable to the clinician, since by only indirectly raising GH levels, the hormone's release profile remains, at least in part, under the control of the body's own regulatory feedback systems, and fluctuations in the levels of circulating GH are damped over time. Additionally, the compounds of the present invention may themselves be administered by sustained release mechanisms. It is also recognized that patients sometimes inadvertently skip doses, and various technologies exist to provide continuous dosing via the digestive tract including, for example, osmotic systems. In this regard, the pharmaceutical compositions of the invention are preferably administered according to the technology disclosed in U.S. Pat. No. 4,612,008.

In the preferred practice of the invention, compounds show selectivity for the sst2 receptor compared with other receptor subtypes, for example sst1, sst3, sst4 and sst5. This selectivity minimizes the chance that other molecular biological or biochemical pathways will be adversely affected while growth hormone secretion is being upregulated. Most preferably, the affinity of a compound for the sst2 type receptor should be at least about 10 times greater than for receptors of the other sst-subtypes.

It should be noted that the compounds of the invention may work by more than one mechanism, including those unrelated to interaction at an sst-type receptor, and the utility of the present compounds in the practice of the invention, including for use in treating other disease states not particularly mentioned herein, is not limited by any particular theory as described herein or by those theories that is generally recognized by those skilled in the art.

Additionally, the compounds of the present invention may interact beneficially with sst-type receptors other than sst2, and may provide therapeutic benefits by acting as somatostatin agonists, rather than antagonists, at sst2 or other sst-type receptors.

As aforementioned, the compounds of this invention include all conformational isomers (eq., cis and trans isomers, whether or not involving double bonds), tautomers, and all optical isomers of compounds of the formula I (e.g., enantiomers and diastereomers), as well as racemic, diastereomeric and other mixtures of all such isomers.

With respect to the design of the compounds of the invention, particular features involving conformational and optical isomerism are of note.

In connection with the above general formula, particular structural features are of note. In formula 1, Additionally, where substitution by one or more halo groups is permitted above, a preferred example is by one or two halo atoms. Preferably the halo atom(s) is selected from chlorine and fluorine. Generally speaking, trifluoromethyl is the preferred species of trifluoro($C_1$–$C_6$)alkyl group. Where substitution by one or more trifluoromethyl groups is permitted, it is preferred that only a single trifluoromethyl group be incorporated.

Additionally, many of the groups of the present compounds may be optionally substituted. As aforementioned, such substituents contribute properties useful to production, storage, or use of the inventive compounds as pharmaceuticals, or at least does not substantially negate their pharmacological activity. It will be appreciated that selection of optional substituents is further guided by principles recognized in the art, and/or is capable of validation through the use of the assays described in the present specification.

Preferred Structural Features

Group Z may exist in the form of various optical isomers. In the below structures (i) to (iv), optically active centers are indicated.

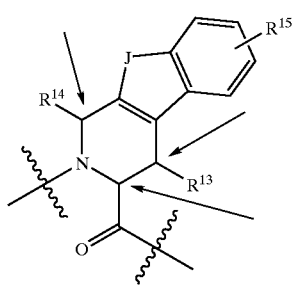

(i)

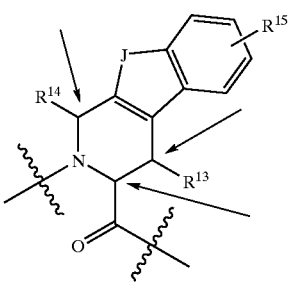

(i)

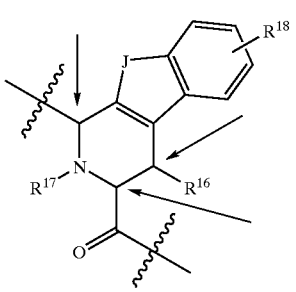

(ii)

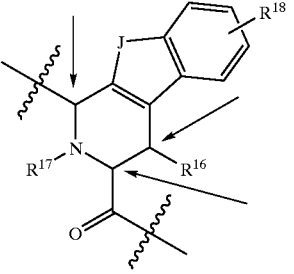

(ii)

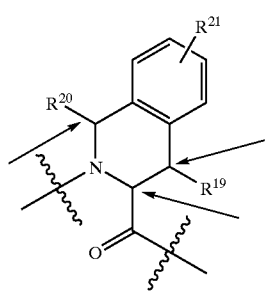

(iii)

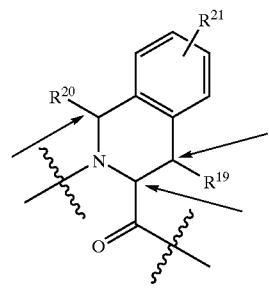

(iii)

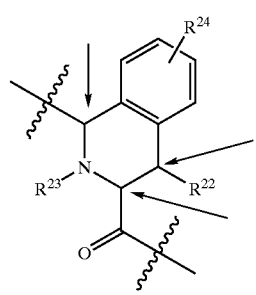

(iv)

(iv)

According to the practice of the invention it is preferred, but not required, that the L-configuration be present at the carbon atom in the carboline provided by the alpha-carbon of the component tryptophan, and similarly that the L-configuration be present at the carbon atom of 1,2,3,4-tetrahydroisoquinoline that is provided by the alpha-carbon of component phenylalanine, both as indicated below.

With respect to the remaining optically active centers, each resultant optically active species is an example of the present invention.

Referring to structures (i) and (ii), J may be S, O, —NH—, or $NCH_3$. Such structures Z may be prepared by the Pictet-Spengler reaction from amino acids that are commercially available, or are readily prepared.

According to a still further embodiment of the invention, group Z may be more broadly defined (group Z') than as otherwise presented herein. In a group Z', the exemplified $(C_1-C_9)$heteroaryl group of structures Z(i) or Z(ii), that is, indole, benzofuran, or benzothiophene is subject to replacement by any other ($C_1$–$C_9$)heteroaryl group within the definition thereof as aforementioned, which group may be also be optionally substituted. Similarly for group Z', the exemplified ($C_6$–$C_{10}$) aryl group (phenyl) in structures Z(iii) and Z(iv) may be replaced with naphthyl, which may also be optionally substitutued.

When group "W" of formula (I) is option (a), it is preferred that this group thereof have a stereospecificity at the indicated position (which corresponds to the α-carbon of an amino acids), such that L-amino acids, or other structures having the same absolute stereospecificity, are defined.

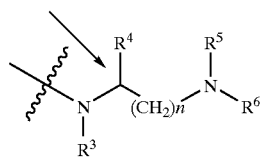

In preferred examples, the W group defines an L-lysine group or a ($C_1$–$C_8$)alkyl ester thereof. In further preferred examples, the W group is L-diaminopimelic acid, L-canavanine, L-ornithine, L-2,4-diaminobutyric acid, L-5-hydroxylysine, L-epsilon-N-methyllysine, or ($C_1$–$C_8$)alkyl esters thereof. In further preferred examples, the W group is an L-arginine group or a ($C_1$–$C_8$)alkyl ester thereof.

In an additional embodiment of the invention, group W according to formula (a) is replaced by L-histidine, L-3-methylhistidine, or an ($C_1$–$C_8$)alkyl ester thereof, even though such structures are not derivable from the depicted formula.

Again with respect to group W option (a), in a preferred example, $R^3$ is selected from option (ii) or option (iii) thereof

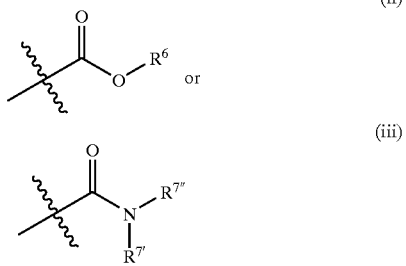

and each of $R^6$, $R^{7'}$ and $R^{7''}$, if present, is ($C_1$–$C_6$) alkyl, for example, methyl, ethyl, and t-butyl.

When the "Z" component is a β-carbolene (for example a "bridged tryptophan"), such as options (i) and (ii), the "W" component is preferably selected from L-lysine or a ($C_1$–$C_8$) alkyl ester thereof, L-diaminopimelic acid, L-canavanine, L-ornithine, L-2,4-diaminobutyric acid, L-5-hydroxylysine, L-epsilon-N-methyllysine, or ($C_1$–$C_8$)alkyl esters of any thereof.

Similarly, when the "Z" component is a tetrahydroisoquinoline (for example, a "bridged phenylalanine"), such as options (iii) and (iv), the "W" component is preferably selected from L-Arginine, or a ($C_1$–$C_8$)alkyl ester thereof. For the purposes of the invention, tetrahydroisoquinolines can be formed using, for example, 2-fluorophenylalaninyl-, 3-fluorophenylalaninyl-, 4-fluorophenylalaninyl- or diphenylalaninyl-.

Alternatively, group W can represent option (b) moiety, wherein structures such as the following are preferred (refer to Schemes 5A, 5B)

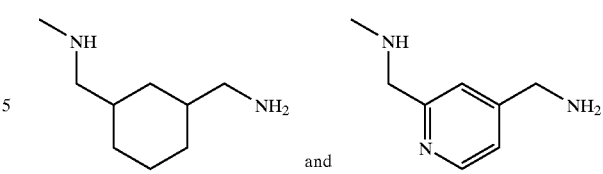

Additionally, many of the groups of the present compounds may be "optionally substituted", as previously defined. As aforementioned, such substituents contribute properties useful to production, storage, or use of the inventive compounds as pharmaceuticals, or at least does not substantially negate their pharmacological activity. It will be appreciated that selection of optional substituents is further guided by principles recognized in the art, and/or is capable of validation through the use of the assays described in the present specification.

Pharmaceutical Formulations

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared, for example, by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In a preferred example of the invention, the compounds of the present invention may be formulated with additional pharmaceutically active substances that directly or indirectly (1) facilitate production and storage in cells of additional growth hormone, or precursor polypeptides thereof, or (2) facilitate release of GH. Such additional substances include growth hormone releasing peptide (GHRP), growth hormone releasing hormone (GHRH), pituitary adenylate cyclase activating polypeptide (PACAP), dopaminergic agonists (e.g. bromocriptine), beta-adrenergic agonists (e.g. isoproterenol) and alpha 1-adrenergic agonists (e.g. methoxamine). For background information see E. O Soyoola et al., *Proceedings of the Society for Experimental Biology & Medicine,* 207(1), pp. 26–33, 1994; V. Locatelli et al., *Pediatric Research,* 36(2), pp. 169–74, 1994; and B. Velkeniers et al., *Journal of Endocrinology,* 143(1), pp. 1–11, 1994.

Equivalently, the additional pharmaceutically active substances may be provided as a separate formulation which is co-administered, or administered at some other timepoint(s) in the course of treatment.

This invention also encompasses pharmaceutical compositions containing prodrugs of compounds of the formula 1. This invention also encompasses methods of treating or preventing disorders that can be treated or prevented by decreasing the levels of somatostatin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula 1. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will also appreciate that when using the compounds of the invention in the treatment of a specific disease, that the compounds of the invention may be combined with various existing therapeutic agents used for that disease, or for other metabolically related or unrelated disease states that may occur simultaneously. As aforementioned, the additional pharmaceutically active substances may be provided as a separate formulation which is co-administered, or administered at some other timepoint(s) in the course of treatment.

The compounds of the invention can also be used in combination with existing therapeutic agents such as the above-mentioned growth hormone secretagogues for the treatment of growth hormone deficiency.

For the treatment of growth hormone deficiency, the compounds of the invention may be combined with agents such as recombinant growth hormone which is marketed by Genentech and licensees (Neutropin, Genotropin and Protropin), Bio-Technology General and licensees (Zomacton, Growject, Elvetium and SciTropin), Novo Nordisk (Norditropin), LG Chem (Eutropin), Ares Serono (Saizen and Serostim), Eli Lilly Co (Humatrope), Monsanto (Posilac brand of bovine growth hormone) and Alpharma (Reporcin brand of swine growth hormone).

The compounds of the invention can also be used in combination with existing therapeutic agents such as Geref (sermorelin, GHRH) from Serono Laboratories Inc.

The compounds of the invention can also be used in combination with existing therapeutic agents such as anabolic steroids, e.g. androisoxazol androstanolone (DHT, dihydrotestosterone, Stanolone, Anabolex, Andractrim), bolandiol, bolasterone, bolazin, boldenone (Equipoise), calusterone, clostebol (chlortestosterone, Steranabol, Alfa Trofodermin, Dermanabol, Trofodermin, Trofoseptine), danazol (Cyclomen, Danocrine), dehydrochlormethyltestosterone (turinabol, Oral-turinabol), drostanolone (dromostanolone, Drolban, Masterid, Masteril, Masteron, Metormon, Premastril), estradiol, ethylestrenol, fluoxymesterone (Halotestin, Ora-Testryl, Android-F), formebolone, furazabol (Miotolon), mestanolone, mesterolone (Proviron, Pluriviron), methandienone (methandrostenolone, Metaboline), methandriol, methenolone (Primobolan), methyltestosterone (Methandren, Premarin with methyltestosterone, Android, Oreton, Testred, Methyltestosterone tabs, Geri-Bons, Geri-tabs, Dermonal), mibolerone (Cheque), nandrolone (Deca-Durabolin, Durabolin, Nandrabolin, Anabolin, Androlone, Hybolin, Nandrobolic), norclostebol, norethandrolone (Nilevar), oxabolone, oxandrolone (Anavar), oxymesterone (Oranabol), oxymetholone (Anapolon 50, Androyd, Anadrol, Anasteron, Dynasten, Oxitosona, Plenastril, Synasteron, Zenalosyn), penmesterol, prasterone, quinbolone, stanozolol (Winstrol, Winstrol-V, Stromba, Strombaject), stenbolone, testosterone (Malogen, Delatestryl, Malogen, Neo-pause, PMS-testosterone Enanthate, Andriol, Duogex, Neo-Pause, Climacteron, Orchisterone-P, Oreton Anadiol, Anatest, Testos-100, Heifer-aid, Synovex-H), tibolone, trenbolone (Parabolan, Finaject) or zeranol.

The compounds of the invention can also be used in combination with existing therapeutic agents such as Somazon (mecasermin, recombinant insulin-like growth factor I) from Fujisawa.

For the treatment of older patients with osteoporosis, suitable agents to be used in combination with the compounds of the invention include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with osteoporosis agents such as lasofoxifene, raloxifene, droloxifene or fosomax and immunosuppressant agents such as FK-506 and rapamycin.

The compounds of the present invention may also be used in combination with immunostimulant agents for the treatment of reduced immune function.

The compounds of the present invention may also be used in combination with fertility agents such as human menopausal gonadotropin, chorionic gonadotropin, follicle stimulating hormone, nafarelin, triptorelin, cetrorelix, and ganirelix for the treatment of infertility.

The compounds of the present invention may also be used in combination with AIDS therapies for the treatment of AIDS-related complex.

The compounds of the present invention may also be used in combination with anti-tumor necrosis factor agents such as infliximab (TNF monoclonal antibody) or etanercept (soluble TNF receptor) for the treatment of cachexia.

The compounds of the present invention may also be used in combination with potassium channel blockers, beta-blockers, anticoagulants or vasodilators for the treatment of heart disease.

The compounds of the present invention may also be used in combination with angiotensin II (ATII) antagonists or erythropoietin for the treatment of renal failure.

For administration to livestock, the compounds of the invention may also be used in combination with feed additives such as antibiotics (e.g. monensin, lasalocid, salinomycin, semduramicin, narasin, maduramicin, virginiamycin, polymixin, efrotomycin, avoparcin, lincomycin, bacitracin, bambermycins, novobiocin, erythromycin, oleandomycin, streptomycin, tylosin, penicillin, tetracycline, oxytetracycline, chlortetracycline, carbadox, olaquindox, neomycin, moenomycin, avilamycin, and flavophospholipol), repartitioning agents, beta-agonists (e.g. Paylean, ractopamine, from Elanco), and also amiterol, bambuterol, biolterol, broxaterol, buphenine, carbuterol, cimaterol, clenbuterol, clorprenaline, colterol, denopamine, dioxethedrine, dioxifedrine, dobutamine, dopexamine, doxaminol, etanterol, fenoterol, flerobuterol, formoterol, hexoprenaline, ibuterol, imoxiterol, isoetarine, isoxsuprine, levisoprenaline, mabuterol, mesuprine, metaterol, methoxyphenamine, nardeterol, orciprenaline, picumeterol, pirbuterol, prenalterol, procaterol, protokylol, quinprenaline, rimiterol, ritodrine, salbutamol, salmeterol, terbutaline, tretoquinol, tulobuterol, xamoterol and zilpaterol.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets, chewable tablets, or capsules prepared by conventional means with pharmaceutically acceptable excipients such as binding agents (eq., pregelatinized maize starch, polyvinylpyrrolidone or hydroxypropyl methylcellulose); fillers (eq., lactose, microcrystalline cellulose or calcium phosphate); lubricants (eq., magnesium stearate, talc or silica); disintegrants (eq., potato starch or sodium starch glycolate); or wetting agents (eq., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (eq., sorbitol syrup, methyl cellulose or hydrogenated edible fats); emulsifying agents (eq., lecithin or acacia); non-aqueous vehicles (e.q., almond oil, oily esters or ethyl alcohol); and preservatives (e.g., methyl or propyl p-hydroxybenzoates or sorbic acid).

For buccal administration, the composition may take the form of tablets or lozenges formulated in conventional manner, or blended with petfood or animal feed, or as a pre-mix for blending with animal feed.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, eq., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human is 0.1 to 100 mg of the active ingredient per unit dose which could be administered, for example, 1 to 4 times per day.

Aerosol formulations for treatment of the conditions referred to above in the average adult human are preferably arranged so that each metered dose or "puff" of aerosol contains 20 $\mu$g to 1000 $\mu$g of the compound of the invention. The overall daily dose with an aerosol will be within the range 0.1 mg to 100 mg. Administration may be several times daily, for example 2, 3, 4 or 8 times, giving for example, 1, 2 or 3 doses each time.

Injected doses are preferably administered from about once a month, up to about 1 to 4 times per day, at an individual dosing of 0.01–1 mg/kg (of active ingredient) and may be intramuscular, intravenous, or subcutaneous, for example.

As is well recognized, the precise dose, and method and timing of administration thereof, are capable of determination by those skilled in the art, and depend upon numerous factors including the activity of the therapeutic compound, the properties of the formulation thereof, the nature and location of the target tissue, and the particulars of the disease state as it exists in a particular patient. Additionally, when the compounds of the present invention are administered to a patient with additional pharmaceutically active substances, one or more pharmaceutical compositions may be used to deliver all of the active agents, which may be administered together, or at different times, as determined by those skilled in the pharmaceutical or medical arts.

The following reaction schemes illustrate preparation of compounds of the present invention. It will be appreciated that certain groups represented by letters ($R_2$, for example) in the Schemes do not always correspond with similarly defined component groups of the formula (I) compounds themselves, since certain functionalities of the reactants are modified, by definition, when the products are formed. $R_1$, $R_2$ and $R_3$ typically represent $(C_1–C_6)$ alkyl groups, whether primary, secondary, or tertiary, but can also be other groups such as $(C_6–C_{10})$aryl or benzyl, for example.
Scheme 1A
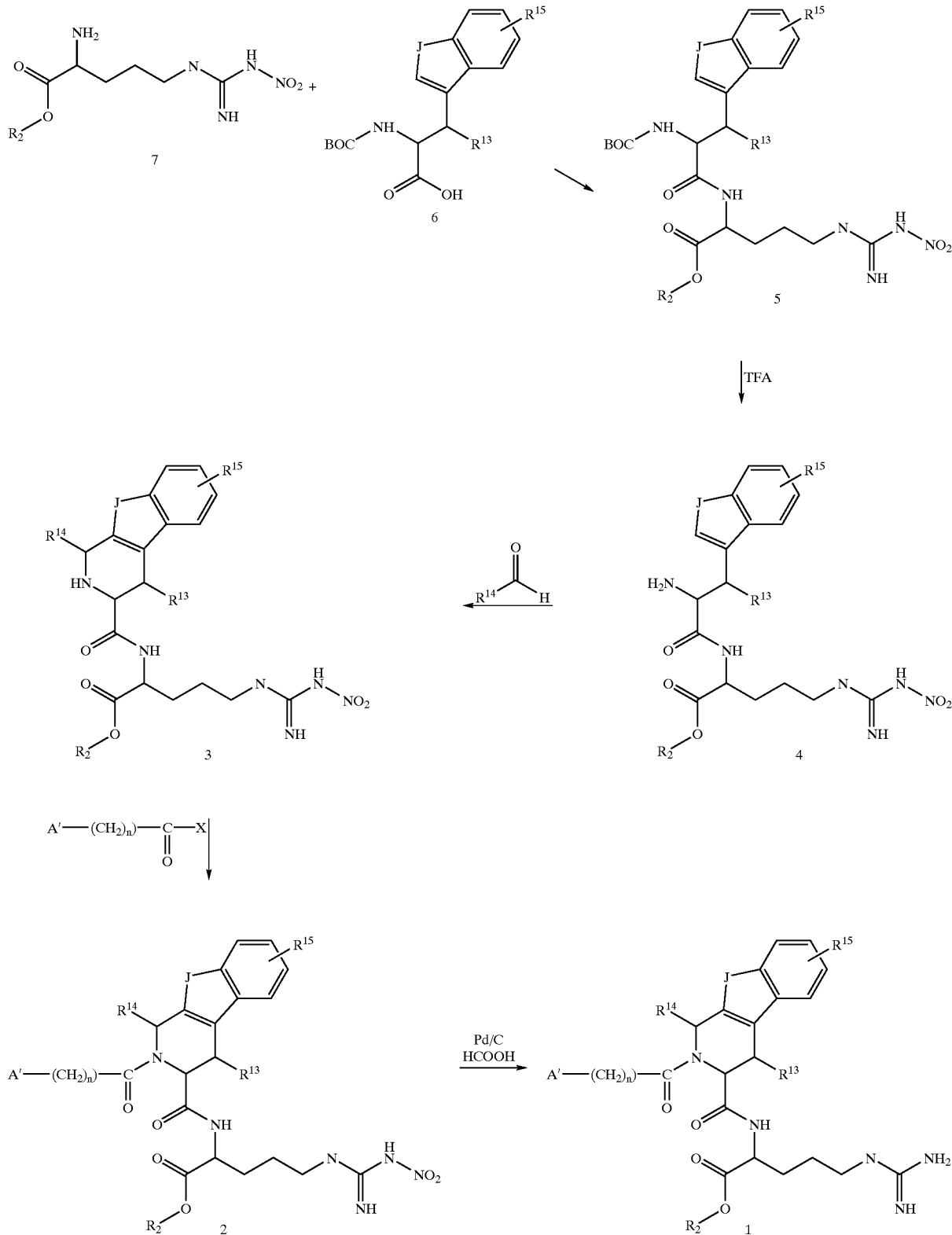

SCHEME 1B
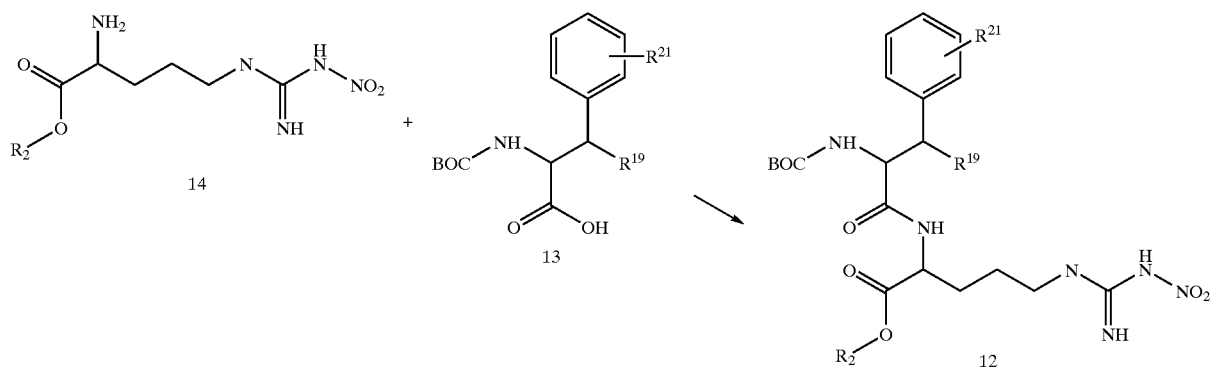
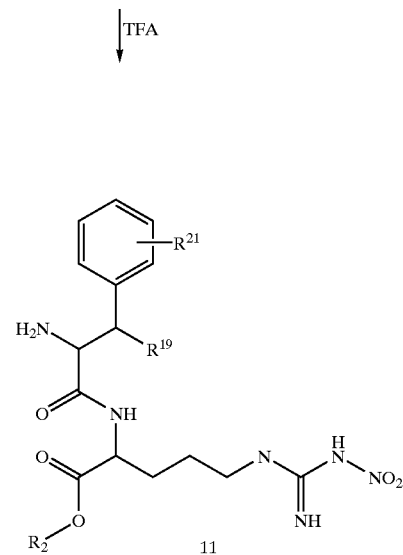
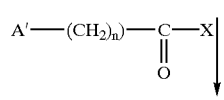
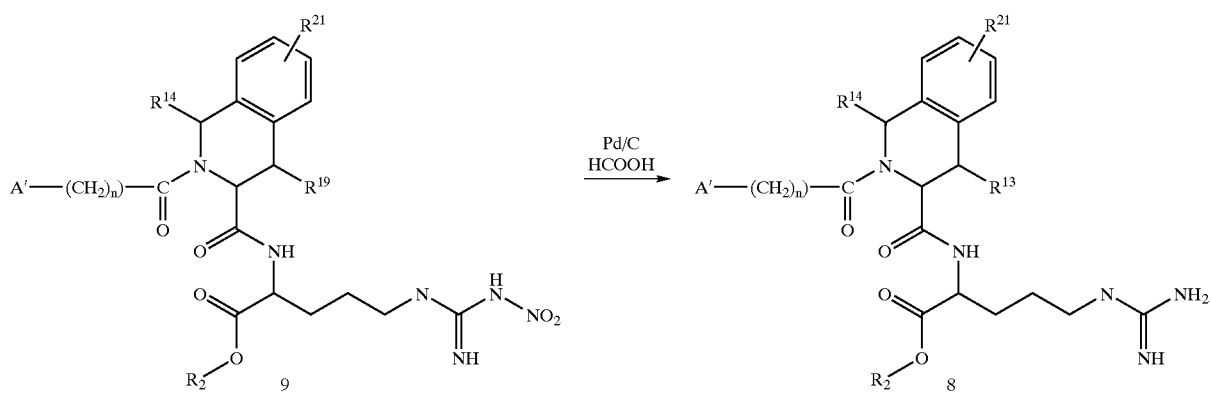

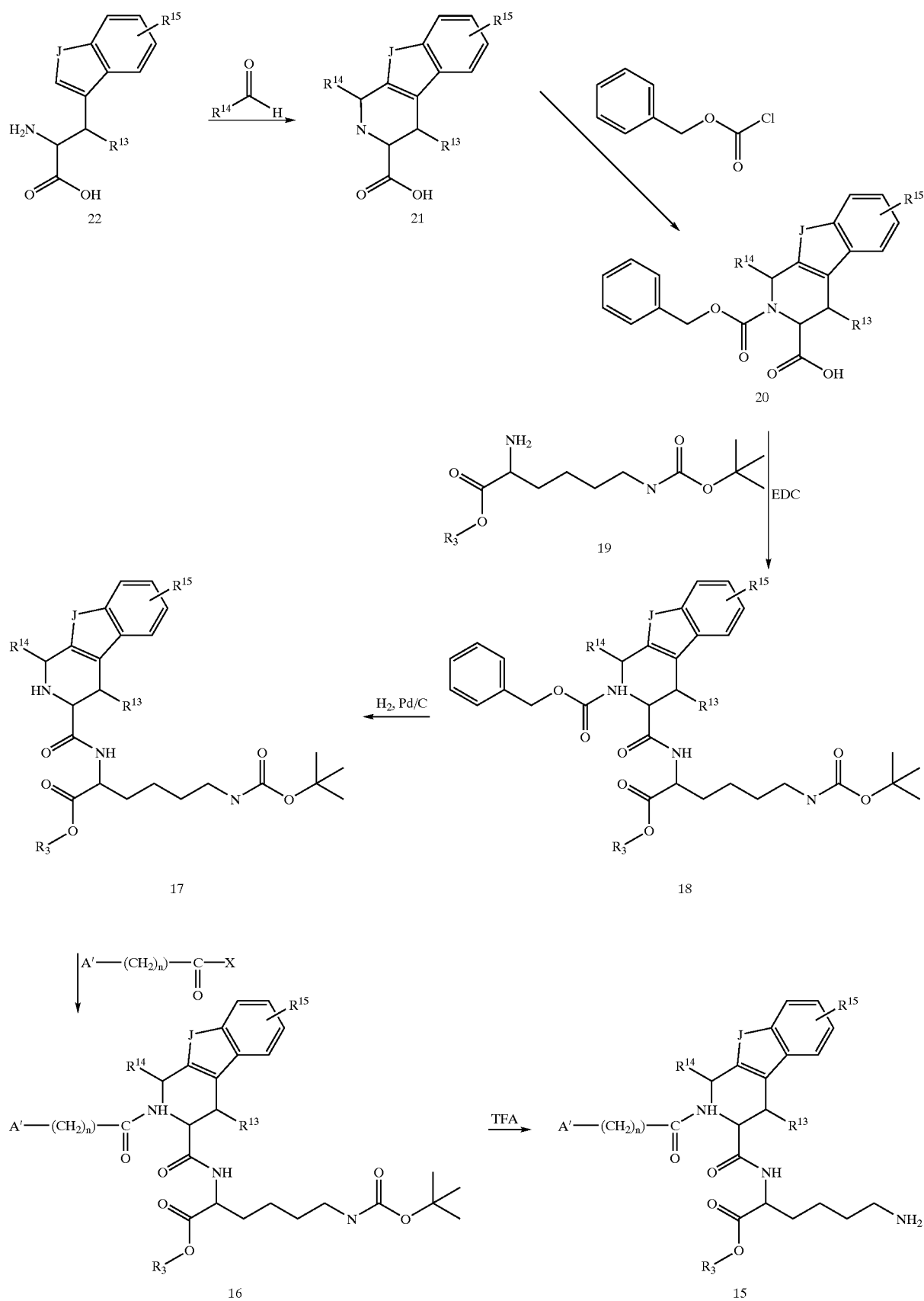

SCHEME 3
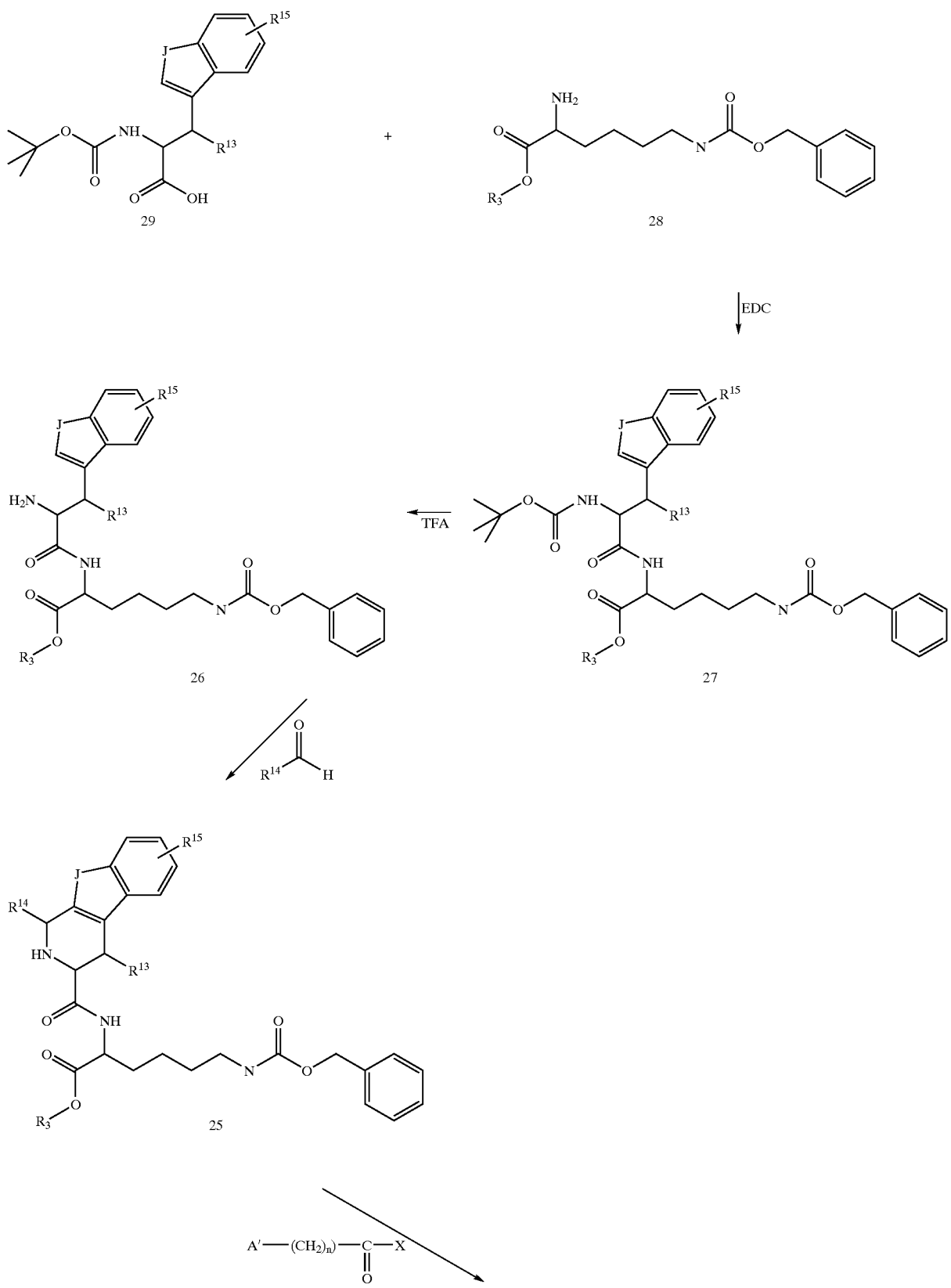

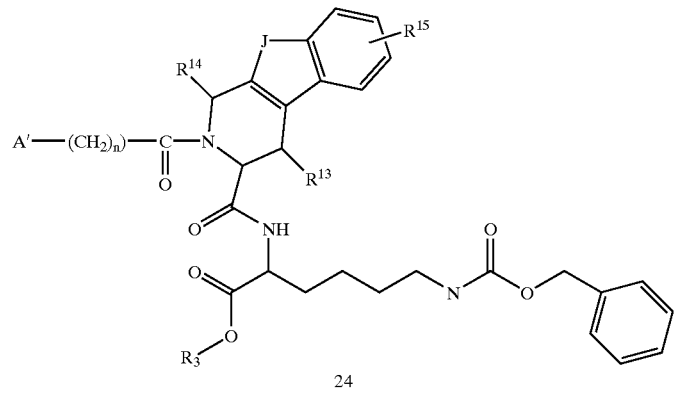
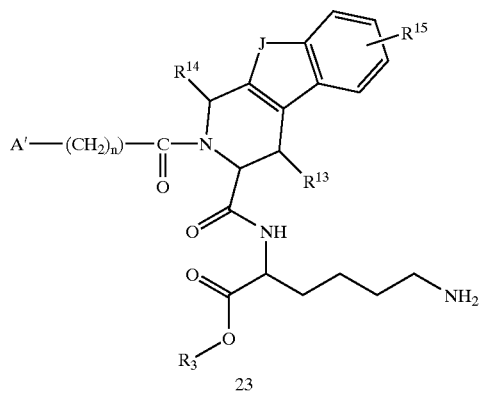
Scheme 4
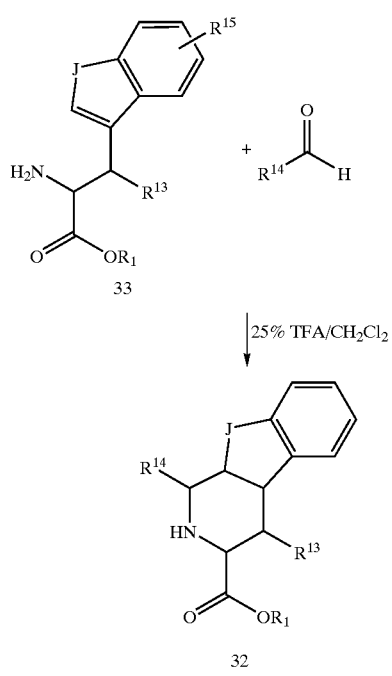
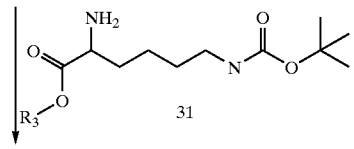
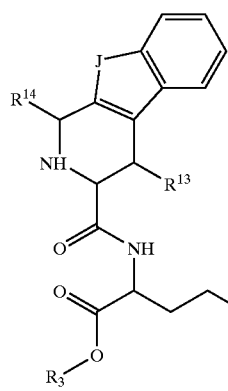

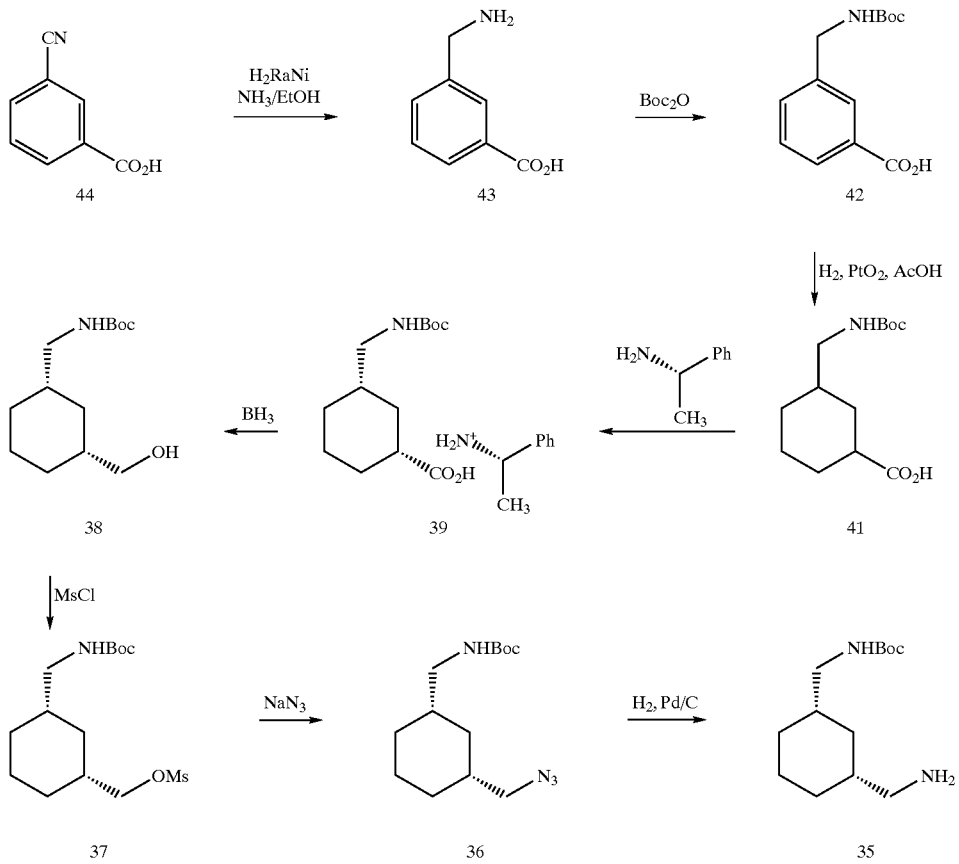

Scheme 5A

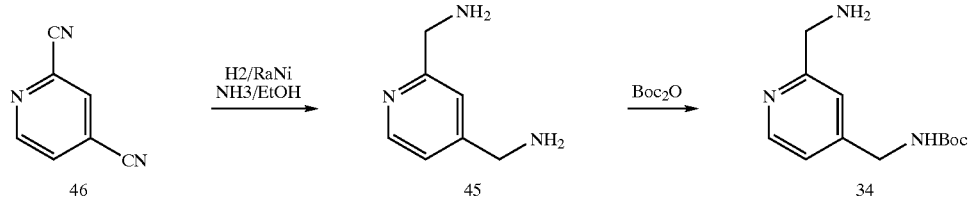

Scheme 5B

General Reaction Conditions

Generally speaking, the compounds of the present invention are made by a series of condensation reactions in which certain reactive groups are appropriately protected, and the sequence of condensation is controlled. Typically, alternative pathways exist to the same products, as the reactants may be coupled in more than one sequence. The starting materials herein are commercially available or are readily prepared. Compounds such as BOC derivatives or CBZ derivatives are also readily prepared.

Referring to Scheme 1A, the compounds of formula 1 which include an L-arginine moiety, may be prepared from the compounds of formula 2 by removal of the guanidine-protecting nitro group via a reduction reaction using formic acids as reducing agent in the presence of palladium on carbon. In a typical procedure, the reaction mixture is stirred overnight under nitrogen, filtered, and the solvent then removed under reduced pressure. Recovered material may then be triturated with diethylether, and dried overnight under high vacuum to yield the final product. Although nitro is the preferred protecting group, Boc may also be used, in which case suitable reaction conditions for deprotection are stirring with trifluoracetic acid or hydrochloric acid.

Again referring to Scheme IA, the compounds of formula 2 may be prepared by reaction of compounds 3 with a compound that provides group A, that is, A'—$(CH_2)_n$—A'—$(CH_2)_nSO_2$—, and A'—$(CH_2)_nCO$—, where n is 0 to 4 ; and wherein A' is selected from ($C_6$–$C_{10}$)aryl-, or ($C_1$–$C_9$) heteroaryl-. Suitable forms of group A include acid chlorides and sulfonyl chlorides which are reacted with compounds 3 under well known conditions. In the case where A is A'—$(CH_2)_n$—, A may first be provided as an A'—$(CH_2)_{n-1}$—CHO group, which is subject to reductive amination on compound 3 using sodium cyanoborohydride.

β-carbolene compounds of formula 3 are prepared from compounds of formula 4 using the appropriate aldehyde by application of Pictet-Spengler reaction. As will be discussed below, the Pictet-Spengler cyclization can be performed at different points depending in the overall scheme. Generally this reaction is conducted under strongly acidic conditions.

Compounds of formula 4 are prepared from compounds of formula 5 by hydrolysis (deprotection) of the BOC group at the α-amino group of the amino acid. Compounds of formula 5 are prepared by condensation of of the compounds of formula 6 and 7, for example in the presence of 1,3-dimethylaminopropyl-3-ethylcarbodiimidehydrochloride (EDC), hydroxybenzotriazole, and dimethylaminopyridine. The reaction mixture may then be washed successfully with portions of of 10% aqueous hydrochloric acid solution, followed by washes with 50% saturated sodium bicarbonate solution, and saturated brine. The resulting product 5 may then be dried over anhydrous magnesium sulfate, filtered, and the solvent removed under reduced pressure.

In the preferred practice of the invention, compounds of formulas 6 and 7 include amino acid moieties which confer peptide-like structure on the final product compounds, consistent with their activity as somatostatin analogs. Compound 7 may represent any one of several suitably protected amino acids wherein the carboxyl groups thereof is protected by a suitable alkyl group ($R_2$). The stereospecificity at this subregion of the product compound, defined as "W" herein, is determined by the stereospecificity of the participating amino acid. In the practice of the invention, stereospecificity corresponding to an L-amino acid is preferred. Compound 6 typically represents a BOC-protected reactant having an indole, benzofuran, or benzothiophene moiety, with a preferred example defining tryptophan or a derivative thereof.

Scheme 1B defines a similar reaction pathway except that reactant 13 represents a BOC-protected phenylalanine, or derivative thereof, and the Pictet-Spengler reaction thus produces a tetrahydroisoquinoline group.

As aforementioned, when the "Z" component is a tetrahydroisoquinoline (a "bridged phenylalanine"), such as Z-options (iii) and (iv), the "W" component is preferably selected from L-Arginine, or a ($C_1$–$C_8$)alkyl ester thereof. For the purposes of the invention, tetrahydroisoquinolines can be formed using, for example, 2-fluorophenylalaninyl-, 3-fluorophenylalaninyl-, 4-fluorophenylalaninyl- or diphenylalaninyl-.

Note that L-lysine is preferably selected to provide the "W" component, when Trp derivatives (whether L or R) as a carbolene are used to provide the "Z" component.

Additionally, when the "Z" component is a β-carbolene (for example, a "bridged tryptophan"), such as Z-options (i) and (ii), the "W" component is preferably selected from L-lysine or a ($C_1$–$C_8$)alkyl ester thereof, L-diaminopimelic acid, L-canavanine, L-ornithine, L-2,4-diaminobutyric acid, L-5-hydroxylysine, L-epsilon-N-methyllysine, or ($C_1$–$C_8$) alkyl esters of any thereof. Under such circumstances, the tryptophan derivative may be L or R, defined at the α-carbon thereof. When the "W" component is so selected, synthesis via a variant of Scheme 1A is preferred. For reaction with compound 6, compound 7 is replaced by a CBZ derivative, in which the alpha carboxy group is also protected.

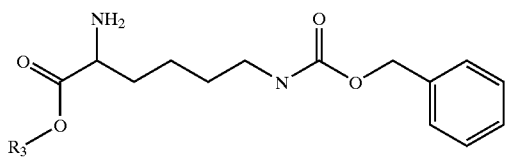

The synthesis is then continued, as outlined in Scheme 1A, except that the final reduction (reaction 2→1) is accomplished using palladium/carbon with $H_2$ to remove CBZ.

Product compounds are also preferably made according to Scheme 3 (product 23), wherein condensation of a CBZ-protected lysine (28) and a BOC-protected heteroaryl amino acid (29) using EDC is depicted. Scheme 3 is also useful where reactant 29 contributes a phenylalanine moiety, with the Pictet-Spengler reaction being similarly conducted as reaction 26→25.

As aforementioned, and indepedent of the general formulas otherwise provided, the W component of the product compound may also define a histidine residue, preferably L-histidine, which may be optionally substituted, preferably by a methyl group, so that W is 2-methylhistidine, for example. Additionally, and making reference to group $R^{10}$, which can modify the W group as otherwise defined herein, the alpha carboxy group of the optionally substituted histidine residue can comprise a ($C_1$–C8)alkyl ester or benzyl ester.

In a variation on the above procedures, the Pictet-Spengler reaction can become the first step in the synthetic pathway. In Scheme 2, compounds 21 are first produced from compounds 22 using this reaction. As before, the reaction is preferably conducted under strongly acidic conditions. The pathway is equally applicable when compound 22 instead represents phenylalanine or a derivative thereof. Product compounds 15 result, and the chemistry described above for attachment of the A group (here 17→16) also applies. Many simple carbolines and tetrahydroisoquinoline caroboxylic acids are commercially available, or are readily prepared.

Referring again to Scheme 2, where Z is defined by option (ii), and $R^{17}$ is, for example, hydrogen,

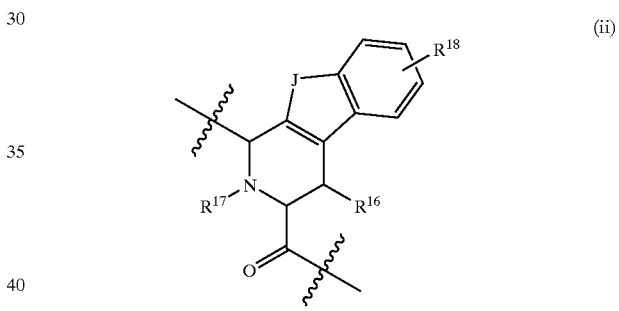

(ii)

it is apparent that compound 17 may also represent essentially the final product of the process. In this case (Scheme 2), the aldehyde $R^{14}$CHO is selected to not only close the ring in the Pictet-Spengler reaction, but also to provide the A group. If the α-amino group of the β-carbolene is present as free NH, the protecting BOC group is then removed from compound 17 under acidic conditions. In the case where the α-amino group of the β-carbolene is alkyated in the final product, the alkyl group is preferably added to compound 17 by reductive deamination of an appropriate aldehyde, followed by reduction with sodium cyanoborohydride. The BOC group is removed under acidic conditions. This approach also works where Z is defined by option (iv).

Scheme 4 is also efficiently used both in cases where group A is to be attached at the nitrogen atom of group Z that is contributed by the amino acid α-amino group, and where attachment of group A is to a ring carbon of Z that is proximal to said nitrogen. In Scheme 4, group $R_1$ of compound 33 represents attachment of the compound to oxime resin (see Example 2). Localizing compounds on the resin facilitates purification procedures and also limits unwanted side reactions. Compounds 32 are produced from compounds 31 by application of the Pictet-Spengler reaction using appropriate aldehyde, $R^{14}$CHO. The overall pathway is similar to that outlined in Scheme 2, except that localization on the oxime resin permits the use of fewer blocking groups on the reactants.

As mentioned similarly for Scheme 2, incorporation of group A into the design of $R^{14}CHO$ permits simultaneous placement of group A, and also ring closure according to the Pictet-Spengler reaction. In such cases, Z groups according to option (ii) thereof are formed, and $R^{14}$ groups A'—$(CH_2)_n$—where n is 0 to 4; and A' is selected from $(C_6-C_{10})$aryl-, and$(C_1-C_9)$heteroaryl- are incorporated. It should be noted however that Scheme 4 is substantially less efficient where group Z is patterned on a phenylalanine moiety as conditions of stronger acidity would typically be needed, releasing reactants from the oxime resin. In such cases, resort to Scheme 2 (using a phenylalanine-containing moiety in the reaction 22→21, under strong acid conditions) is preferred. BOC is removed from compounds 30 under acidic conditions which permit retention of the ester group at $R_3$, if this is desired.

Should the product compound instead include a group A attached at the α-amino group of Z, such may be introduced into compound 30 using a sulfonyl chloride, an acid chloride, or by reductive amination of an appropriate aldehyde, as aforementioned.

Schemes 5A and 5B provide approaches to group "W", in the general structure of formula (I), where W is alternative (b).

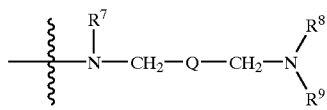

and in particular, outline representative syntheses of component W wherein Q is, for example, either cyclohexane or pyridine. Thus, Schemes 5A and 5B permit synthesis of compounds similar to compounds of Schemes 1–4, but wherein the representative arginine or lysine moiety thereof is replaced by a moiety that includes a cyclohexane or pyridine group, for example.

Referring to Scheme 5A, compounds of formula 35 may be prepared from compounds of 36 by reduction with hydrogen under appropriate conditions. Compounds of formula 36 may be prepared from compounds of formula 37 via reaction using $NaN_3$ to displace the mesylate ester of compounds 37. Compounds 37 may be prepared from compounds 38 with mesyl (methanesulfonyl) chloride under basic conditions, for example, in triethylamine/dichloromethane at 0°C., in good yield. Compounds 38 may be prepared from compounds 39 by reduction at the carboxyl group thereof using $BH_3$. Compounds 39, having the stereospecificity indicated in Scheme 5A, are prepared from racemic compounds 41 by chiral resolution with stereospecific α-methylbenzylamine 40, followed by selective purification, such as by crystallization. Compounds 41 may be prepared from the corresponding aromatic compounds 42 by reduction with hydrogen, for example, under appropriate conditions. Compounds 42 in turn are prepared from the corresponding (unprotected) compounds 43 by reaction with BOC anhydride under standard conditions. Finally, compounds 44 may be prepared from available starting materials 44, by reduction of the cyano group with hydrogen over a Raney nickel preparation. In Scheme III(b), advantage is taken of available starting materials to generate compounds of the formula 34 in 2 steps, first from compounds of formula 45 using BOC anhydride. Compounds 45 are generated from compounds of formula 46 by reduction of both cyano groups, again with hydrogen and Raney nickel as catalyst.

Additional Embodiments of the Invention

In additional embodiments of the invention, group A is replaced by one of the following structures:

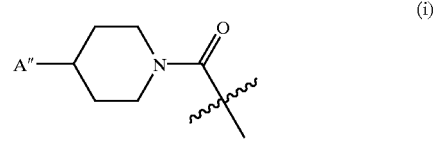
(i)

wherein A" is selected from the groups defined for A' above;

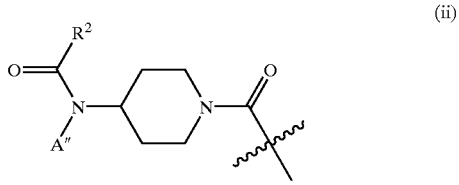
(ii)

wherein $R^2$ is
(a) selected from H, $(C_1-C_8)$alkyl-, and phenyl$(CH_2)$—, wherein said alkyl and phenyl groups are each optionally substituted by one or more halo groups, or
(b) is selected from groups defined for A' above; and
A" is selected from the groups defined for A' above; and

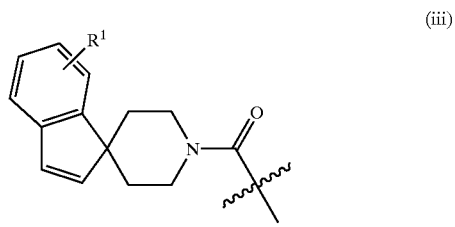
(iii)

wherein each occurrence of $R^1$ is independently selected from hydroxy, halo, $(C_1-C_8)$alkyl- optionally substituted by one or more halo, and $(C_1-C_8)$alkoxy- optionally substituted by one or more halo;

In the practice of the invention, the above compounds were less effective than some of the aforementioned compounds under the particular assay conditions chosen.

The following are representative compounds of the invention.

EXAMPLE 1

5-Guanidino-2{[2-(toluene-4-sulfonyl)-1,2,3,4-tetrahydro-isoquinoline-3-carbonyl]-amino{-pentanoic acid methyl ester Preparation of Tos-L-Tic 993 mg (24.8 mmole) sodium hydroxide was dissolved in 50 mL of water, after which 2.00 gm (11.29 mmol) of S-1,2,3,4-tetrahydro-3-isoquinoline carboxylic acid (Tic) was added with stirring until dissolved. A solution of 2.152 gm (11.29 mmole) tosyl chloride in 50 mL of diethyl ether was then added, and the 2 phase reaction stirred vigorously overnight. The aqueous layer was separated out and acidified to pH 2.0 with 10% aqueous hydrochloric acid. The product was then extracted with three 100 mL portions of diethyl ether, and the combined organic layers were washed with saturated sodium chloride, dried over magnesium sulfate, and then filtered. The solvent was removed under reduced pressure to yield 3.367 gm (90%) of product.

Step 2

To a solution of 100 mg of Tos-L-Tic (0.30 mmol), 122 mg of Arg(NO$_2$)—OMe HCl (0.45 mmol), 61 mg of hydroxybenzotriazole (0.39 mmol), and 184 mg of 4-dimethylaminopyridine (1.51 mmol) in 50 mL of methylene chloride as added 174 mg (0.78 mmol) of 1,3-dimethylaminopropyl-3-ethylcarbodiimide hydrochloride. After stirring for 15 hours, 100 mL of additional methylene chloride was added to the reaction, and it was washed three times with 30 mL portions of 10% aqueous hydrochloric acid solution, then twice with 20 mL of 50% saturated sodium bicarbonate solution, and finally once with 20 mL of saturated brine. The product was then dried over anhydrous magnesium sulfate, filtered, and the solvent removed under reduced pressure. The product was next dissolved in 20 mL of methanol, and 230 mg of 10% palladium on carbon was added under nitrogen, followed by addition of 1 mL of formic acid, after which the reaction stirred for 15 hours. The catalyst was filtered off, and the solvent was then removed rapidly under reduced pressure to yield 22 mg of product. This material can also be synthesized by coupling a suitably protected arginine fragment with a suitably protected Tic fragment, deprotecting the Tic amino group, condensing this material with p-toluenesulfonyl chloride, and finally, deprotecting the arginine sidechain.

EXAMPLE 2

General Procedure for Synthesis of β-carbolene Analogs.

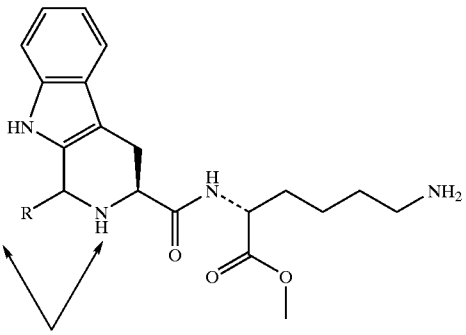

possible group A positions

Oxime resin (Novabiochem, 0.6 mmol,g; 150 mg. 0.09 mmol) was placed into a 10 mL Bio-Rad (Richmond, Calif.) poly-prep column and washed sequentially with CH$_2$Cl$_2$ (3 times×5 mL), dimethylformamide (2 times×5 mL), and CH$_2$Cl$_2$ (3 times×5 mL), respectively. Then, a solution consisting of N-Boc-L-Trp (109 mg, 0.36 mmol), DIC (diisopropylcarbodiimide, 0.36 mmol, 69 mg), and 10% DMAP (dimethylaminopyridine, 5 mg, 0.036 mmol) in 3 ml of CH$_2$Cl$_2$. was added, and the mixture was agitated by rotation at room temperature for 16 hours. The mixture was then washed sequentilly with CH$_2$Cl$_2$ (3 times×5 mL), DMF (2 times×5 mL), ethanol (2 times×5 mL), and finally CH$_2$Cl$_2$ (3 times×5 mL). 3 mL of 25% TFA in CH$_2$Cl$_2$ was then added, and the mixture rotated for 30 minutes, followed by washing with CH$_2$Cl$_2$ (3 times×5 mL), DMF (2 times×5 mL), 10% DIEA in CH$_2$Cl$_2$ (diisopropylethylamine, 2 times×5 mL), ethanol (2 times×5 mL), and finally CH$_2$Cl$_2$ (3 times×5 mL).

At this point, the synthesis continues with step 33→32 of Scheme 4. A solution of aldehyde R$^{14}$CHO (0.9 mmol, 10 equiv to reactant 33) in 25% TFA in CH$_2$Cl$_2$ (3 mL) was added, and rotated for 6 h. The mixture was then washed sequentially with CH$_2$Cl$_2$ (3 times×5 mL), DMF (2 times×5 mL), 10% DIEA in CH$_2$Cl$_2$ (2 times×5 mL), ethanol (2 times×5 mL), and CH$_2$Cl$_2$ (3 times×5 mL), respectively. A solution of H-Lys(Boc)OMe.HCl (94 mg, 0.36 mmol) and triethylamine (50 uL, 0.36 mmol) in 3 ml CH$_2$Cl$_2$ was then added, followed by rotation at room temperature for 48 hours. The contents of the tube were then filtered and concentrated. The crude product material was further purified on a Biotage Quad 3 system (1:3 hexane:ethyl acetate) to isolate 10–40% product. Resulting products were stirred in 4 M HCl in dioxane for 20 minutes, concentrated, and tritrated with isopropylether to deliver the HCl salts.

EXAMPLE 3

6-Amino-2{[1-(3-benzyloxy-phenyl)2,3,4,9-tetrahydro-1H-β-carboline-3-carbonyl]-amino}-hexanoic acid methyl ester Following generally the procedure of Example 2, the compound was prepared from 3-benzyloxybenzaldehyde to give 24 mg of a 1.9:1 mixture of cis:trans adducts. MS (APCI) M+541.6.

A sample of cis and trans isomers was separated by HPLC to give 8 mg of the cis isomer, 6-Amino-2-{[1-(S)-(3-benzyloxy-phenyl)-2,3,4,9-tetrahydro-1H-β-carboline-3-carbonyl]-amino}-hexanoic acid methyl ester, and 3.5 mg of the corresponding trans adduct 6-Amino-2-}[1-(R)-3-benzyloxy-phenyl)-2,3,4,9-tetrahydro-1H-β-carboline-3-carbonyl]-amino}-hexanoic acid methyl ester.

EXAMPLE 4

6-Amino-2-{[2-(toluene-4-sulfonyl)-2,3,4,9-tetrahydro-1H-β-carboline-3-carbonyl]-amino}-hexanoic acid methyl ester Step 1

Initial preparation of 6-tert-Butoxycarbonylamino-2(S)-[(2,3,4,9-tetrahydro-1H-β-carboline-3-(S) carbonyl)-amino]-hexanoic acid methyl ester.

L-norharmane (β-carbolene, 1.08 g, 5 mmol) was added to a solution of 1N NaOH (20 mL) and saturated NaHCO$_3$ (20 mL), followed by sonication until completely dissolved. Benzyl chloroformate (1 mL, 7 mmol) was added and the resulting solution was stirred overnight. The aqueous phase was washed with ether (2 times×25 mL), acidified to pH 1, and extracted with CH$_2$Cl$_2$ (3 times×50 mL). The combined extracts were dried (MgSO$_4$) and evaporated to give 1.56 g 1,3,4,9-tetrahydro-β-carboline-2,3-dicarboxylic acid 2-benzyl ester. The acid (1.4 g, 4 mmol) was dissolved into CH$_2$Cl$_2$ (30 mL) and TEA (1 mL, 8 mmol), after which EDC (1,3-dimethylaminopropyl-3-ethylcarbodiimide hydrochloride, 802 mg, 4.2 mmol) and H-L-Lys(Boc)-OMe (1.24 g, 4.2 mmol) were added. After stirring overnight, the mixture was diluted with water (50 mL) and extracted with CH$_2$Cl$_2$ (3 times×50 mL). The combined extracts were washed sequentially with citric acid, saturated NaHCO$_3$ and brine solutions, dried over (MgSO$_4$), and evaporated to give 1.82 g of dipeptide. A sample (1.2 g, 2 mmol) of the CBZ-protected dipeptide was combined with Pd/C (25 mg, 0.2 mmol) in ethanol (20 mL) and agitated under H$_2$ (40 psi) overnight. The resulting mixture was filtered through celite and evaporated to deliver 0.961 product, 6-tert- Butoxycarbonylamino-2-(S)-[(2,3,4,9-tetrahydro-1H-β-carboline-3-(S)-caronyl)-amino]-hexanoic acid methyl ester, MS (APCI) M+459.6

Step 2

A solution of 6-tert-Butoxycarbonylamino-2-(S)-[(2,3,4,9-tetrahydro-1H-β-carboline-3-(S)-carbonyl)-amino]-hexanoic acid methyl ester (37 mg, 0.08 mmol), TEA (0.21 mL, 0.15 mmol) and toluene-4-sulfonyl chloride (19 mg, 0.1 mmol) in $CH_2Cl_2$ (2 mL) wa stirred at room temperature overnight. The mixture was diluted with water (10 mL), extracted with $CH_2Cl_2$, washed with brine, dried (over $MgSO_4$) and evaporated to give 39 mg crude product. Purification by flash chromatography ($SiO_2$ gel; 2:1 EtOAc/hexanes) delivered 24 mg pure Boc-protectected product. A sample (15 mg) of this material was stirred in a 50% solution of TFA in $CH_2Cl_2$ for 30 minutes and evaporated to afford 12 mg of the TFA salt. MS (APCI) M+513.5.

EXAMPLE 5

6-Amino-2-{[2-(biphenyl-4-sulfonyl)-2,3,4,9-tetrahydro-1H-β-carboline-3-carbonyl]-amino}-hexanoic acid methyl ester 6-Amino-2-{[2-(biphenyl-4-sulfonyl)-2,3,4,9-tetrahydro-1H-β-carboline-3-carbonyl]-amino}-hexanoic acid methyl ester was prepared according to the above procedure from 6-tert-Butoxycarbonylamino2-(S)-[(2,3,4,9-tetrahydro-1H-β-carboline-3-(S)-carbonyl)-amino]-hexanoic acid methyl ester (37 mg, 0.08 mmol) and biphenyl-4-sulphonyl chloride (24 mg, 0.1 mmol) to deliver 6 mg of the TFA salt. MS (APCI) M+575.5

EXAMPLE 6

6-Amino-2-{[2-(biphenyl-4-carbonyl)-2,3,4,9-tetrahydro-1H-β-carboline-3-carbonyl]-amino}-hexanoic acid methyl ester A solution of 6-tert-butoxycarbonylamino-2-(S)-[(2,3,4,9-tetrahydro-1H-β-carboline-3-(S)-carbonyl)-amino]-hexanoic acid methyl ester (37 mg, 0.08 mmol), TEA (0.1 mL, 0.12 mmol), PPAA (n-propane phosphonic acid cyclic anhydride, 64 ul, 50% solution in EtOAc, 0.1 mmol) and 4-phenyl benzoic acid (20 mg, 0.01 mmol) in $CH_2Cl_2$ (2 mL) was stirred overnight at room temperature. The mixture was diluted with water (10 mL), extracted with $CH_2Cl_2$, washed with brine, dried ($MgSO_4$) andthen evaporated to give 39 mg crude product. Purification by flash chromatography ($SiO_2$ gel; 2:1 EtOAc/hexanes) delivered 22 mg pure Boc-protected product. A sample (14 mg) of this material was stirred in a 50% solution of TFA in $CH_2Cl_2$ for 30 minutes and evaporated to afford 12 mg of the TFA salt. MS (APCI) M+539.5.

EXAMPLE 7

6-Amino-2-[(2-biphenyl-4-yl-methyl-2,3,4,9-tetrahydro-1H-β-carboline-3-carbonyl)-amino] hexanoic acid methyl ester 6-tert-butoxycarbonylamino-2-(S)-[(2,3,4,9-tetrahydro-1 H-β-carboline-3-(S)-carbonyl)-amino]-hexanoic acid methyl ester (23 mg, 0.05 mmol), 4-phenyl benzaldehde (14 mg, 0.075 mmol) and $NaCNBH_3$ (7 mg, 0.1 mmol) were stirred in methanol (5 mL) overnight. The mixture was filtered through celite and evaporated. The resulting residue was taken up in $CH_2Cl_2$, washed with water and then brine, dried ($MgSO_4$), and evaporated to afford 33 mg crude amine. Purification by flash chromatography ($SiO_2$ gel; 1:1 ETOAc/hexanes) delivered 18 mg Boc-protected adduct. A sample (15 mg) of this material was stirred in 50% TFA in $CH_2Cl_2$ for 30 minutes and evaporated to give 15 mg of the TFA salt. MS (APCI) M+525.4.

EXAMPLE 8

6-Amino-2-({1-[4-(4-trifluoromethyl-phenoxy)-phenyl]-2,3,4,9-tetrahydro-1H-β-carboline-3-carbonyl}-amino)-hexanoic acid methyl ester Following generally the procedure of Example 2, the compound was prepared from 4-(4-trifluoromethyl-phenoxy)-benzaldehyde to give 21 mg of a 1.7:1 mixture of cis:trans adducts MS M+595.6.

EXAMPLE 9

6-Amino-2-{[-1-(4-butyl-phenyl)-2,3,4,9-tetrahydro-1H-β-carboline-3-carbonyl]-amino}-hexanoic acid methyl ester Following generally the procedure of Example 2, the compound was prepared from 4-n-butylbenzaldehyde to give 6 mg of product. MS M+491.6.

EXAMPLE 10

6-Amino-2-{[1-(4-pyrrolidin-1-yl-phenyl-2,3,4,9-tetrahydro-1H-β-carboline-3-carbonyl]-amino}-hexanoic acid methyl ester Following generally the procedure of Example 2, the compound was prepared from 4-pyrrolidin-1-yl-benzaldehyde to give 10 mg of a 1.8:1 mixture of cis:trans adducts. MS M+504.2.

EXAMPLE 11

6-Amino-2-({1-[2-(4-isopropyl-phenyl)-1-methyl-ethyl]2,3,4,9-tetrahydro-1H-β-carboline-3-carbonyl}-amino)-hexanoic acid methyl ester Following generally the procedure of Example 2, the compound was prepared from 3-(4-lsopropyl-phenyl)-2-methyl-propionaldehyde to give 3.5 mg of a mixture of cis:trans adducts. MS M+519.5.

EXAMPLE 12

6-Amino-2-({1-[3-(4-trifluoromethyl-phenoxy)-phenyl]-2,3,4,9-tetrahydro-1H-β-carboline-3-carbonyl}-amino)-hexanoic acid methyl ester Following generally the procedure of Example 2, the compound was prepared from 3-(4-trifluoromethyl-phenoxy)-benzaldehyde to give 4 mg of a 1.6:1 mixture of cis:trans isomers. MS M+595.6.

EXAMPLE 13

6-Amino-2-{[1-(1-methyl-3-phenyl-butyl)-2,3,4,9-tetrahydro-1H-β-carboline-3-carbonyl]-amino}-hexanoic acid methyl ester Following generally the procedure of Example 2, the compound was prepared from 1-methyl-3-phenyl-butanal to give 5 mg of product as a mixture of isomers. MS M+505.1.

EXAMPLE 14

6-Amino-2-{[2-(toluene-4-sulfonyl)-2,3,4,9-tetrahydro-1H-β-carboline-3-carbonyl]-amino}-hexanoic acid tert-butyl ester 6-Amino-2{[2-(toluene-4-sulfonyl)-2,3,4,9-tetrahydro-1H-β-carboline-3-carbonyl]-amino}-hexanoic acid tert-butyl ester was prepared from 6-Amino-2-{[2-(biphenyl-4-sulfonyl)-2,3,4,9-tetrahydro-1H-β-carbolnyl]-amino}-hexanoic acid tert-butyl ester (25 mg) and toluene-4-sulfonyl according to the above procedures to deliver 15 mg of the TFA salt. MS (APCI) M+555.5.

EXAMPLE 15

5-Guanidino-2-{[2-(toluene-4-sulfonyl)-1,2,3,4-tetrahydro-isoquinoline-3-carbonyl]-amino}-pentanoic acid tert-butyl ester

EXAMPLE 16

6-Amino-2-({2-[4-(2-oxo-2,3-dihydro-benzoimidazol-1-yl)-piperidine-1-carbonyl]-2,3,4,9-tetrahydro-1H-β-carboline-3-carbonyl}-amino)-hexanoic acid tert-butyl ester

EXAMPLE 17

6-Amino-2-({2-[(1H-indol-3-yl)-acetyl]-2,3,4,9-tetrahydro-1H-β-carboline-3-carbonyl}-amino)-hexanoic acid methyl ester A solution of 6-tert-butoxycarbonylamino-2-(S)-[2,3,4,9-tetrahydro-1H-□-carboline-3-(S)-carbonyl-amino]hexanoic acid methyl ester (23 mg, 0.05 mmol), TEA (20 ul, 0.2 mmol), PPAA (propanephosphonic acid cyclic anhydride, 35 ul, 50% solution in EtOAc, 0.1 mmol) and (1H-Indol-3-yl)-acetic acid (20 mg, 0.07 mmol) in $CH_2Cl_2$ (2 mL) was stirred overnight at room temperature. The mixture was diluted with water (10 mL), extracted with $CH_2Cl_2$, washed with brine, dried ($MgSO_4$) and then evaporated to give 31 mg crude product. Purification by flash chromatography (SiO2 get; 2:1 EtOAc/hexanes) delivered 18 mg pure Boc-protected product. A sample (5 mg) of this material was stirred in a 50% solution of HCl in EtOH for 30 minutes and evaporated to afford 5 mg of the HCl salt. MS (APCI) M+516.4.

EXAMPLE 18

6-Amino-2-{[1-(4-isopropyl-phenyl)-2,3,4,9-tetrahydro-1H-β-carboline-3-carbonyl]-amino}-hexanoic acid methyl ester Following generally the procedure of Example 2, the compound was prepared from 3-I-propyl-benzaldehyde to give 3 mg of a 1:1mixture of cis:trans adducts. MS M+476.6.

EXAMPLE 19

6-Amino-2-{[1-(3-trifluoromethyl-phenyl)-2,3,4,9-tetrahydro-1H-β-carboline-3-carbonyl]-amino}-hexanoic acid methyl ester Following generally the procedure of Example 2, the compound was prepared from 4-(3-trifluoromethyl-phenoxy)-benzaldehyde to give 4 mg of a 1.6:1 mixture of cis:trans adducts MS M+595.6.

EXAMPLE 20

6-Amino-2-[(1-anthracen-9-yl-2,3,4,9-tetrahydro-1H-β-carboline-3-carbonyl)-amino]-hexanoic acid methyl ester Following generally the procedure of Example 2, the compound was prepared from anthracene-9-carbaldehyde. 8 mg of a 2.7:1 mixture of cis:trans adducts was recovered. MS (APCI) M+535.6.

Biological Assays

Various types of somatostain agonists are well known in the art, and the capacity of a compound of the present invention to act as an agonist, an antagonist, or as either, depending on physiological circumstances, can be predicted from the assays which are known in the art and/or described below. For example, measurement of cyclic-AMP, growth hormone release, microphysiometry responses, cell proliferation or protein kinase activity can be measured in cultured pituitary cells, cell lines or other cells such as neuroblastoma cells that express somatostatin receptors, and cells transfected with recombinant somatostatin receptors including transfected yeast cells. (Y. C. Patel et al., *Biochemical & Biophysical Research Communications*, 198(2), pp. 605–612, 1994; M. G. Cattaneo et al., *FEBS Letters*, 397 (2–3), pp. 164–168, 1996; J. A. Koenig et al., *British Journal of Pharmacology*, 120(1), pp. 45–51, 1997; D. Djordjijevic et al., *Endocrinology*, 139(5), pp. 2272–2277, 1998; W. R. Baumbach et al., *Molecular Pharmacology*, 54(5), pp. 864–73, 1998).

Generally, somatostatin or agonists thereof demonstrate inhibitory activity, hence a stimulus is first applied (e.g. forskolin for cyclic-AMP) and the inhibitory effect of somatostatin observed. Antagonists reverse the inhibitory effects of somatostatin.

The ability of compounds of formula (I), and the pharmaceutically acceptable salt, solvates or hydrate thereof (hereinafter referred to as the compounds of the present invention) to act as somatostatin antagonists, or agonists, and consequently to demonstrate their effectiveness in the treatment of disease states, is shown by the following assays.

EXAMPLE 21

Bovine ("b")sst2 Binding Assay

The present example describes an assay for binding of pharmaceutically useful somatostatin agonists and antagonists at the bovine sst2 receptor.

The methods for culturing Neuro2A cells and measuring competitive binding potency ($IC_{50}$) were similar to those described by J. A. Koenig et al., "Somatostatin receptors in Neuro2A neuroblastoma cells: operational characteristics", *British J. Pharmacol.*, 120, 45–51, 1997, with the following modifications.

Binding assays were conducted 72 hours after transiently transfecting the Neuro2A cells with a plasmid (PCI-bsst2) containing an insert coding for the bovine sst2 receptor, placed downstream of the cytomegalovirus promoter. In the transfection step, $6.5 \times 10^6$ Neuro2A cells were added in 35 ml of media to each tissue culture flask (162 $cm^2$ surface area). The next day, transfection was conducted using Fugene 6 (Boehringer Mannheim, 1 814 443) according to the manufacturer's directions. The Fugene 6 (30 μl/flask) was equilibrated with 8 μg of PCI-bsst2 plasmid, and added to the Neuro2A cells in the absence of fetal bovine serum. After 3 hours, fresh serum-containing media was added. The assay buffer was modified to contain 50 mM HEPES, 5 mM $MgCl_2$, 1 mg/ml bovine serum albumin (BSA), 0.02 mg/ml bacitracin, and 10 μM each of aprotinin, leupeptin and AEBSF. The transfected Neuro2A cells were dissociated in the absence of trypsin/EDTA, in ice cold assay buffer (5.5 ml/flask), and cells were homogenized in a 55 ml Wheaton Dounce homogenizer (15–20 strokes). Membrane preparations were stored in aliquots at −70°C. Competitive binding assays and separation of bound from free radioactivity were conducted in polyethyleneimine-soaked Millipore 96 Well GF/C Filterplates, (MAFC NOB10). An amount of membrane was used that bound approximately 20% of [$^{125}$I]-somatostatin 14 tracer (Amersham, IM161), which was added to all wells at 15,000 cpm/well (approximately 15 nCi/well). Somatostatin was included in each experiment as positive control, at 7 concentrations from 0.0042 to 1.667 nM, and test compounds were included at 7 concentrations from 33 nM to 13.33 $\mu$M. The reaction volume was 300 $\mu$l and the incubation was conducted for 1 hour at 37°C. Non-specific binding was defined using 0.83 $\mu$M somatostatin 14. The incubation was terminated by vacuum filtration through the glass fiber plate bottom, followed with a 250 $\mu$l wash with assay buffer minus BSA and protease inhibitors. The plate bottom was then sealed, scintillation fluid was added (Wallac Supermix, 250 $\mu$l/well), and radioactivity was measured in a 96 well microtiter liquid scintillation counter.

IC$_{50}$ values are determined by polynomial regression and analzyed using a MACRO program. An IC$_{50}$ value of less than about 5 $\mu$M is preferred.

EXAMPLE 22

Rat Pituitary Assay for Somatostatin Receptor Antagonists

This assay is designed to quantitate the activity of antagonists of somatostatin that interact directly at the somatostatin receptor. The assay facilitates discovery of agents which increase growth hormone secretion by modulating the inhibitory effects of somatostatin. As aforementioned, somatostatin (also abbreviated SRIF) inhibits GH secretion in the anterior pituitary by binding to a high affinity membrane-bound (and G-protein coupled) receptor which is coupled negatively to adenyl cyclase, thereby reducing intracellular levels of cAMP that would otherwise facilitate, for example, secretion/release of GH from cytoplasmic granules. Vasoactive intestinal peptide (VIP) is one of several endogenous peptides that stimulates GH secretion by binding to a high affinity membrane-bound receptor coupled to a G protein-dependent signal transduction pathway. VIP activates adenylate cyclase and produces increased intracellular cAMP levels. These peptides may be involved in the coordinate regulation of GH secretion under physiologic conditions and be mediated through cAMP. The cell line used in the screen is a clonal pituitary cell that synthesizes and secretes GH in response to VIP and SRIF, and many other regulatory hormones, as expected for normal pituitary cells. The screen is designed to quantitate the ability of test agents to reverse SRIF's inhibition of the elevated intracellular cAMP levels produced by VIP.

In particular, cyclic AMP (cAMP) content of the pituitary cell line GH$_4$C$_1$ was used to differentiate somatostatin agonists from antagonists. The method was similar to that described by L. J. Dorflinger et al. ("Somatostatin inhibits vasoactive intestinal peptide-stimulated cyclic adenosine monophosphate accumulation in GH pituitary cells", *Endocrinology*, 113, pp. 1541–50, 1983 ) with the following modifications. Aliquots (50 $\mu$l ) of GH$_4$C$_1$ cell suspension at 1–2 million cells/ml were added to 50 $\mu$l of each solution of test compound in Adenylyl Cyclase Activation FlashPlate® Assay plates from NEN™ Life Science Products (catalog SMP004A). Putative somatostatin agonists or antagonists were typically tested at concentrations of 10, 1 and 0.1 $\mu$M, in the presence of 100 nM vasoactive intestinal peptide (VIP; Sigma V3628) and 10 nM somatostatin 14 (cell culture tested, Sigma S1763). The FlashPlates®, which are coated with antibody against cAMP and contain scintillant integral to the plastic, are supplied as part of a kit with all necessary reagents to estimate cAMP content of whole cell preparations, including Stimulation Buffer, Detection Buffer, cAMP Standard, and [$^{125}$I]-cAMP Tracer. This afforded a convenient way to conduct a homogenous immunoradiometric assay of cAMP content in cells lysed in situ, following incubation of the cells with test compound. cAMP content in the GH$_4$C$_1$ cells was determined according to the manufacturer's instructions, by comparison with standards at concentrations from 10 to 1,000 nM cAMP. In this assay, VIP increased cAMP content of the GH$_4$C$_1$ cells, and somatostatin caused a partial inhibition. Test compounds acting as somatostatin antagonists were detected by their tendency to increase cAMP content in comparison to control wells containing VIP and somatostatin but no test compound. Somatostatin agonists conversely decreased cAMP content.

IC$_{50}$ values are determined by polynomial regression and analzyed using a MACRO program. An IC$_{50}$ value of less than about 5 $\mu$M is preferred.

EXAMPLE 23

Effect of a Somatostatin Antagonist on GH Release in 12 kg Pigs

Studies indicate that concentrations of GH increase in small pigs within 10 minutes of administration of somatostatin antagonists, and then return to pre-treatment levels within 40 minutes post-administration.

The following protocol describes the effects of various doses of a somatostatin antagonist on release of endogenous porcine GH (or pST, porcine somatatrophin). Methods used to evaluate effects of compounds on plasma GH concentrations in barrows (castrated male pigs) were similar to those reported by M. J. Estienne et al., "Methyl-D,L-aspartate-induced growth hormone secretion in barrows: possible mechanisms of action", *Journal of Animal Science* 74, pp. 597–602, 1996, with the following modifications. Forty cross-bred barrows weighing approximately 12 kg were acclimatized for 2 days at 10 pigs per 36 sq. ft. pen, 4 pens per study, with feed (PS-9 swine starter diet) and water provided ad libitum. To enhance uniformity, two pigs/pen were eliminated based on being smallest or largest, or for health reasons, bringing the group size to 8 pigs/treatment. An equal number of pigs in each pen received 1 of 4 possible treatments at random, i.e. one of 3 doses of test compound or diluent alone. Compounds diluted in approximately 1 ml/pig sterile saline were administered by intramuscular injection into the rear leg (ham), about 1 minute after collection of the first blood sample into 7 ml heparinized evacuated tubes via jugular venepuncture. Blood samples were similarly collected at 10 minute intervals up to 40 minutes after injection of test compound or diluent. Plasma was separated by centrifugation and frozen at −20° C.).

EXAMPLE 24

RIA Procedure for Determination of GH Levels in Plasma.

The present assay is used to determine GH levels (for example, porcine GH or canine GH) in plasma samples.

The double antibody radioimmunoassay (RIA) used to determine porcine GH concentrations in plasma samples was similar to that described by Y. N. Sinha et al., "Studies of GH secretion in mice by a homologous radioimmunoassay for mouse GH", *Endocrinology,* 91, pp.784–92, 1972, and that of F. Cocola et al., "A rapid radioimmunoassay method of growth hormone in dog plasma", *Proceedings of the Society for Experimental Biology and Medicine,* 151, pp. 140–14, 1976. Modifications were as follows. Native porcine GH (pGH) for radioiodination as tracer, canine GH for use as standard (cGH; AFP-1983B; the aminoacid sequence of canine and porcine GH are the same), and primary antibody (monkey anti-cGH; AFP-21452) were supplied by A. F. Parlow, Harbor UCLA Medical Center. Recombinant porcine GH from Biogenesis was alternatively used for radioiodination as tracer. Radioiodinations were conducted by Biomedical Technologies Inc, Stoughton, Mass. Primary antibody (1:50,000 or 1:100,000 final dilution), normal monkey serum (ICN 55988; 1:1,000 final dilution), and plasma sample or standard (0.08 to 2.5 ng cGH/tube) were mixed and incubated for 2 hours at ambient temperature, then tracer (10,000 cpm/tube) was added and the incubation continued for a further 20 hours at ambient temperature in a total volume of 500 μl. Secondary antibody (goat anti-monkey IgG ICN 55418; final dilution 1:160) and polyethyleneglycol 8,000 (final concentration 44 mg/ml) were added and mixed in a final volume of 1.6 ml. Tubes were incubated at 4° C. for 2 hours with shaking, then they were centrifuged, supernates discarded, and the gamma-emission of the pellets determined.

Plasma growth hormone concentrations, expressed as ng/ml, were calculated from the standard line following log-logit transformation.

What is claimed is:

1. A compound according to the formula

A—Z—W    (formula I)

or a pharmaceutically acceptable salt, solvate, or hydrate thereof; wherein

A is selected from the groups consisting of:

A'—$(CH_2)_n$—, A'—$(CH_2)_n SO_2$—, and A'—$(CH_2)_n CO$—, where n is 0 to 4; and A' is selected from
  (a) $(C_6-C_{10})$aryl-, selected from phenyl or naphthyl; or
  (b) $(C_1-C_9)$heteroaryl-, selected from the group consisting of furyl-, thienyl- thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl- pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5, 6, 7, 8-tetrahydro-quinolin-3-yl, benzoxazolyl, benzothiazolyl, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl- quinolyl-, phthalazinyl-, quinoxalinyl-, quinazolinyl-, and benzoxazinyl-;
  wherein said A' group (a) or (b) is optionally substituted by zero to seven groups, each independently selected from:
  hydroxy, halo, amino, trifluoromethyl-, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$alkyl(difluoromethylene)$(C_1-C_3)$alkyl-, $(C_1-C_6)$acylamino$(C_1-C_6)$alkyl-, $(C_1-C_6)$alkoxy$(C_1-C_6)$acylamino-, amino$(C_1-C_6)$acyl-, amino$(C_1-C_6)$acyl$(C_1-C_6)$ alkyl-, $(C_1-C_6)$alkylamino$(C_1-C_6)$acyl-, $((C_1-C_6)$alkyl$)_2$amino$(C_1-C_6)$acyl-, $(C_3-C_{10})$cycloalkyl$(C_1-C_6)$alkyl-, $(C_1-C_6)$acyloxy$(C_1-C_6)$alkyl-, $(C_2-C_6)$alkoxy$(C_1-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_1-C_9)$heteroaryl$(C_1-C_6)$alkoxy$(C_1-C_6)$alkyl-, $(C_1-C_6)$alkylthio$(C_1-C_6)$alkyl-, $(C_6-C_{10}$ )arylthio$(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, $(C_1-C_6)$alkyl(difluoromethylene)-, $(C_1-C_3)$alkyl(difluoromethylene)$(C_1-C_3)$alkyl-, $(C_1-C_6)$alkoxy$(C_1-C_6)$acyl-, $(C_1-C_6)$alkylamino$(C_1-C_6)$acyl-, $((C_1-C_6)$alkyl$)_2$amino$(C_1-C_6)$acyl-, $(C_6-C_{10})$aryl-, $(C_1-C_9)$heteroaryl-, $(C_6-C_{10})$aryl$(C_1-C_6)$alkyl-, $(C_1-C_9)$heteroaryl$(C_1-C_6)$alkyl-, $(C_6-C_{10})$aryl$(C_6-C_{10})$aryl-, $(C_6-C_{10})$aryl$(C_6-C_{10})$aryl$(C_1-C_6)$alkyl-, $(C_3-C_{10})$cycloalkyl-, $(C_3-C_6)$cycloalkyl$(C_1-C_6)$alkyl-, $(C_3-C_{10})$heterocycloalkyl-, $(C_3-C_{10})$heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_1-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6$alkyl-, $((C_1-C_6)$alkyl$)_2$amino$(C_1-C_6)$alkyl-;

Z is selected from group (i)

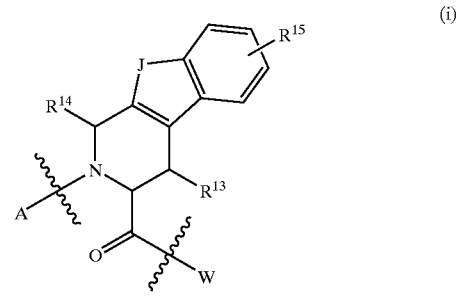

where $R^{13}$ is H, or $(C_1-C_6)$alkyl optionally substituted by one or more halo groups;

$R^{14}$ is H, $(C_1-C_6)$alkyl, trifluoro$(C_1-C_6)$alkyl-, or phenyl $(CH_2)$—, wherein said alkyl and phenyl groups are each optionally substituted by one or more halo groups, or $R^{14}$ is selected from the groups A above, optionally substituted by one or more halo groups;

$R^{15}$ is selected from hydrogen, hydroxy, halo, $(C_1-C_6)$alkyl- optionally substituted by one or more halo, and $(C_1-C_6)$alkoxy- optionally substituted by one or more halo; and J is S, O, —NH—, or $NCH_3$;

W is (a):

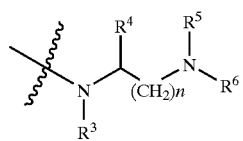

(a)

wherein n is 2–5, $R^3$ and $R^6$ are independently selected from H, $(C_1-C_8)$ alkyl-, phenyl $(CH_2)$-, wherein said alkyl and phenyl groups are optionally substituted by one or more halo groups;

$R^4$ is selected from H, $(C_1-C_8)$alkyl-, and phenyl$(CH_2)$-, wherein said alkyl and phenyl groups are optionally substituted by one or more halo groups;or is

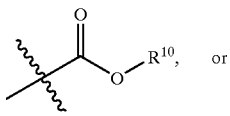

(1)

or

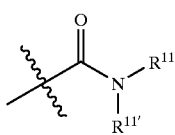

(2)

where groups $R^{10}$, $R^{11}$ and $R^{11'}$ are each, independently, selected from H, $(C_1-C_8)$alkyl-, and phenyl$(CH_2)$—, wherein said alkyl and phenyl groups are optionally substituted by one or more halo groups;

$R^5$ is H, $(C_1-C_8)$alkyl-, and phenyl$(CH_2)$-, wherein said alkyl and phenyl groups are optionally substituted by one or more halo groups; or is

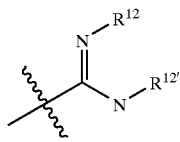

wherein $R^{12}$ and $R^{12'}$ are each independently selected from H, $(C_1-C_8)$alkyl-, and phenyl$(CH_2)$—, wherein said alkyl and phenyl groups are optionally substituted by one or more halo groups;

or W is (b)

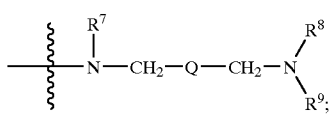

(b)

wherein Q is selected from the group consisting of:

(i) $(C_6-C_{10})$aryl-, selected from phenyl or naphthyl;

(ii) $(C_1-C_9)$heteroaryl-, selected from the group consisting of furyl-, thienyl- thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5, 6, 7, 8-tetrahydro-quinolin-3-yl, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl- quinolyl-, phthalazinyl-, quinoxalinyl-, quinazolinyl-, and benzoxazinyl-;

(iii) $(C_3-C_{10})$cycloalkyl that is selected from the group consisting of cyclopropyl-, cyclobutyl-, cyclopentyl-; cyclohexyl-, cycloheptyl-, cyclopropenyl-, cyclobutenyl- cyclopentenyl-, cyclohexenyl-, cycloheptenyl-, 1,3-cyclobutadienyl-, 1,3-cyclopentadienyl-, 1,3-cyclohexadienyl-, 1,4-cyclohexadienyl-1,3-cycloheptadienyl-, 1,4-cycloheptadienyl-, 1,3,5-cycloheptatrienyl- bicyclo[3.2.1]octane, bicyclo[2.2.1] heptane and the norborn-2-ene unsaturated form thereof; and (iv) $(C_3-C_{10})$heterocycloalkyl that is selected from the group consisting of pyrrolidinyl-, tetrahydrofuranyl- dihydrofuranyl-, tetrahydropyranyl-, pyranyl-, thiopyranyl-, aziridinyl-, oxiranyl-, methylenedioxyl-, chromenyl-, isoxazolidinyl-, 1,3-oxazolidin-3-yl- isothiazolidinyl-, 1,3-thiazolidin-3-yl-, 1,2-pyrazolidin-2-yl-, 1,3-pyrazolidin-1-yl-, piperidinyl-, thiomorpholinyl-, 1,2-tetrahydrothiazin-2-yl-, 1,3-tetrahydrothiazin-3-yl-, tetrahydrothiadiazinyl-, morpholinyl-, 1,2-tetrahydrodiazin-2-yl-, 1,3-tetrahydrodiazin-1-yl-, tetrahydroazepinyl-, piperazinyl-, and chromanyl;

and $R^7$, $R^8$, and $R^9$ are each independently selected from H, $(C_1-C_8)$alkyl-, and phenyl$(CH_2)$—, wherein said alkyl and phenyl groups are optionally substituted by one or more halo groups.

2. The compound of claim 1, wherein group A' is a $(C_6-C_{10})$ aryl group selected from phenyl and naphthyl.

3. The compound of claim 1, wherein group A' is a $(C_1-C_9)$ heteroaryl group that is selected from the group consisting of furyl-, thienyl-, thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5, 6, 7, 8-tetrahydro-quinolin-3-yl-, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl-, quinolyl-, phthalazinyl-, quinoxalinyl-, quinazolinyl-, and benzoxazinyl-.

4. The compound of claim 1, wherein group A' is optionally substituted by one to five groups, each independently selected from the group consisting of hydroxy, halo, amino, trifluoromethyl, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$ acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$ alkyl(difluoromethylene)$(C_1-C_3)$alkyl-, $(C_1-C_6)$acylamino $(C_1-C_6)$alkyl-, $(C_1-C_6)$alkoxy$(C_1-C_6)$acylamino-, amino $(C_1-C_6)$acyl-, amino$(C_1-C_6)$acyl$(C_1-C_6)$alkyl-, $(C_1-C_6)$ alkylamino($C_1$–$C_6$)acyl-, (($C_1$–$C_6$)alkyl)$_2$amino($C_1$–$C_6$) acyl-, ($C_3$–$C_{10}$)cycloalkyl($C_1$–$C_6$)alkyl-, ($C_1$–$C_6$)acyloxy ($C_1$–$C_6$)alkyl-, ($C_2$–$C_6$)alkoxy($C_1$–$C_6$)alkyl-, piperazinyl ($C_1$–$C_6$)alkyl-, ($C_1$–$C_6$)acylamino($C_1$–$C_6$)alkyl-, ($C_6$–$C_{10}$) aryl($C_1$–$C_6$)alkoxy($C_1$–$C_6$)alkyl-, ($C_2$–$C_9$)heteroaryl ($C_1$–$C_6$)alkoxy($C_1$–$C_6$)alkyl-, ($C_1$–$C_6$)alkylthio($C_1$–$C_6$) alkyl-, ($C_6$–$C_{10}$)arylthio($C_1$–$C_6$)alkyl-, ($C_1$–$C_6$)alkylsulfinyl ($C_1$–$C_6$)alkyl-, ($C_6$–$C_{10}$)arylsulfinyl($C_1$–$C_6$)alkyl-, ($C_1$–$C_6$) alkylsulfonyl($C_1$–$C_6$)alkyl-, ($C_6$–$C_{10}$)arylsulfonyl($C_1$–$C_6$) alkyl-, amino($C_1$–$C_6$)alkyl-, ($C_1$–$C_6$)alkylamino($C_1$–$C_6$) alkyl-, ($C_1$–$C_6$)alkyl(difluoromethylene)—, ($C_1$–$C_3$)alkyl (difluoromethylene)($C_1$–$C_3$)alkyl-, ($C_1$–$C_6$)alkoxy($C_1$–$C_6$) acyl-, ($C_1$–$C_6$)alkylamino($C_1$–$C_6$)acyl-, (($C_1$–$C_6$)alkyl)$_2$ amino($C_1$–$C_6$)acyl-, ($C_6$–$C_{10}$)aryl-, ($C_5$–$C_9$)heteroaryl-, ($C_6$–$C_{10}$)aryl($C_1$–$C_6$)alkyl-, ($C_2$–$C_9$)heteroaryl($C_1$–$C_6$) alkyl-, ($C_6$–$C_{10}$)aryl($C_6$–$C_{10}$)aryl-, ($C_6$–$C_{10}$)aryl($C_6$–$C_{10}$) aryl($C_1$–$C_6$)alkyl-, ($C_3$–$C_{10}$)cycloalkyl-, ($C_3$–$C_6$)cycloalkyl ($C_1$–$C_6$)alkyl-, ($C_3$–$C_{10}$)heterocycloalkyl-, ($C_3$–$C_{10}$) heterocycloalkyl($C_1$–$C_6$)alkyl-, hydroxy($C_2$–$C_6$)alkyl-, ($C_1$–$C_6$)acyloxy($C_2$–$C_6$)alkyl-, ($C_1$–$C_6$)alkoxy($C_2$–$C_6$) alkyl-, piperazinyl($C_1$–$C_6$)alkyl-, ($C_1$–$C_6$)acylamino ($C_1$–$C_6$)alkyl- ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$) alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl ($C_1$–$C_6$)alkyl-, ($C_1$–$C_6$)alkylsulfonyl($C_1$–$C_6$)alkyl-, ($C_6$–$C_{10}$)arylsulfonyl($C_1$–$C_6$)alkyl-, amino($C_1$–$C_6$)alkyl-, ($C_1$–$C_6$)alkylamino($C_1$–$C_6$)alkyl-, and (($C_1$–$C_6$)alkyl)$_2$ amino($C_1$–$C_6$)alkyl.

5. The compound of claim 1, wherein group Q of group W, option (b), is a ($C_6$–$C_{10}$) aryl group selected from phenyl and naphthyl.

6. The compound of claim 1, wherein group Q of group W, option (b), is a ($C_1$–$C_9$) heteroaryl group that is selected from the group consisting of furyl-, thienyl- thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl- 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5, 6, 7, 8-tetrahydro-quinolin-3-yl-, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl-, quinolyl-, phthalazinyl-, quinoxalinyl-, quinazolinyl-, and benzoxazinyl-.

7. The compound of claim 1, wherein group Q of group W, option (b), is a ($C_3$–$C_{10}$)cycloalkyl group that is selected from the group consisting of cyclopropyl-, cyclobutyl-, cyclopentyl-, cyclohexyl-, cycloheptyl-, cyclopropenyl-, cyclobutenyl-, cyclopentenyl-, cyclohexenyl-, cycloheptenyl-, 1,3-cyclobutadienyl-, 1,3-cyclopentadienyl-, 1,3-cyclohexadienyl-, 1,4-cyclohexadienyl-, 1,3-cycloheptadienyl-, 1,4-cycloheptadienyl-, 1,3, 5cycloheptatrienyl-, bicyclo[3.2.1]octane-, bicyclo [2.2.1]heptane-, and the norborn-2-ene unsaturated form thereof.

8. The compound of claim 1, wherein group Q of group W, option (b), is a ($C_3$–$C_{10}$)heterocycloalkyl group that is selected from the group consisting of pyrrolidinyl-, tetrahydrofuranyl- dihydrofuranyl-, tetrahydropyranyl-, pyranyl-, thiopyranyl-, aziridinyl-, oxiranyl-, methylenedioxyl-, chromenyl-, isoxazolidinyl-, 1,3-oxazolidin-3-yl-isothiazolidinyl-, 1,3-thiazolidin-3-yl-, 1,2pyrazolidin-2-yl-, 1,3-pyrazolidin-1-yl-, piperidinyl-, thiomorpholinyl-, 1,2-tetrahydrothiazin-2-yl-, 1,3tetrahdrothiazin-3-yl-, tetrahydrothiadiazinyl, morpholinyl-, 1,2-tetrahydrodiazin-2-yl-, 1,3-tetrahydrodiazin-1-yl-, 1,3-tetrahydrodiazin-1-yl-, tetrahydroazepinyl-, piperazinyl-, and chromanyl.

9. The compound of claim 1 wherein component W thereof is an optionally substituted histidine residue.

10. The compound of claim 1, wherein $R^{13}$, is trifluoromethyl.

11. The compound of claim 1 wherein $R^{15}$ is trifluoromethyl.

12. The compound of claim 1 wherein $R^{14}$ is trifluoromethyl.

13. A compound selected from the group consisting of
6-Amino-2-{[2-(toluene-4-sulfonyl)-2,3,4,9-tetrahydro-1H-β-carboline-3-carbonyl]-amino}-hexanoic acid methyl ester;
6-Amino-2-{[2-(biphenyl-4-sulfonyl)-2,3,4,9-tetrahydro-1H-β-carboline-3-carbonyl]-amino}-hexanoic acid methyl ester;
6-Amino-2-{[2-(biphenyl-4-carbonyl)-2,3,4,9-tetrahydro-1H-β-carboline-3-carbonyl]-amino}-hexanoic acid methyl ester;
6-Amino-2-[(2-biphenyl-4-ylmethyl-2,3,4,9-tetrahydro-1H-β-carboline-3-carbonyl)-amino]-hexanoic acid methyl ester;
6-Amino-2-{[2-(toluene-4-sulfonyl)-2,3,4,9-tetrahydro-1H-β-carboline-3-carbonyl]-amino}-hexanoic acid tert-butyl ester;
6-Amino-2-({2-[4-(2-oxo-2,3-dihydro-benzoimidazol-1-yl)-piperidine-1-carbonyl]-2,3,4,9-tetrahydro-1H-β-carboline-3-carbonyl}-amino)-hexanoic acid tert-butyl ester; and
6-Amino-2-({2-[(1H-indol-3-yl)-acetyl]-2,3,4,9-tetrahydro-1H-β-carboline-3-carbonyl}-amino)-hexanoic acid methyl ester.

14. A compound selected from the group consisting of
6-Amino-2-{[4-methyl-2-(toluene-4-sulfonyl)-2,3,4,9-tetrahydro-1H-β-carboline-3-carbonyl]-amino}-hexanoic acid methyl ester;
6-Amino-2-{[4-methyl-2-(toluene-4-sulfonyl)-2,3,4,9-tetrahydro-1H-β-carboline-3-carbonyl]-amino}-hexanoic acid tert-butyl ester;
6-Amino-2-{[2-(biphenyl-4-sulfonyl)-2,3,4,9-tetrahydro-1H-β-carboline-3-carbonyl]-amino}-hexanoic acid tert-butyl ester;
6-Amino-2-{[2-(biphenyl-4-carbonyl)-2,3,4,9-tetrahydro-1H-β-carboline-3-carbonyl]-amino}-hexanoic acid tert-butyl ester;
6-Amino-2-[(2-biphenyl-4-ylmethyl-2,3,4,9-tetrahydro-1H-β-carboline-3-carbonyl)-amino]-hexanoic acid tert-butyl ester;
2-(Toluene-4-sulfonyl-2,3,4,9-tetrahydro-1H-β-carboline3-carboxylic acid (3-aminomethyl-cyclohexylmethyl)-amide;
2-(Toluene-4-sulfonyl)-2,3,4,9-tetrahydro-1H-β-carboline3-carboxylic acid (4-aminomethyl-pyridin-2-ylmethyl)-amide;
2-(Biphenyl-4-sulfonyl)-2,3,4,9-tetrahydro-1H-β-carboline-3-carboxylic acid (3-aminomethyl-cyclohexylmethyl)-amide;
2-(Biphenyl-4-sulfonyl)-2,3,4,9-tetrahydro-1H-β-carboline-3-carboxyl acid (4-aminomethyl-pyridin-2-ylmethyl)-amide;

2-(Biphenyl-4-carbonyl)-2,3,4,9-tetrahydro-1H-β-carboline-3-carboxylic acid (3-aminomethyl-cyclohexylmethyl)-amide;

2-(Biphenyl-4-carbonyl)-2,3,4,9-tetrahydro-1H-β-carboline-3-carboxylic acid (4-aminomethyl-pyridin-2-ylmethyl)-amide;

2-Biphenyl-4-ylmethyl-2,3,4,9-tetrahydro-1H-β-carboline-3-carboxylic acid (3-aminomethyl-cyclohexylmethyl)-amide;

2-Biphenyl-4-ylmethyl-2,3,4,9-tetrahydro-1H-β-carboline-3-carboxylic acid (4-aminomethyl-pyridin-2-ylmethyl)-amide;

6-Amino-2-{[2-(4-methyl-benzoyl)-2,3,4,9-tetrahydro-1H-β-carboline-3-carbonyl]-amino}-hexanoic acid tert-butyl ester;

6-Amino-2-{[2-(4-methyl-benzyl)-2,3,4,9-tetrahydro-1H-β-carboline-3-carbonyl]-amino}-hexanoic acid tert-butyl ester;

6-Amino-2-[(2-benzyl-2,3,4,9-tetrahydro-1H-β-carboline-3-carbonyl)-amino]-hexanoic acid tert-butyl ester;

6-Amino-2-[(2-benzoyl-2,3,4,9-tetrahydro-1H-β-carboline-3-carbonyl)-amino]-hexanoic acid tert-butyl ester; and 6-Amino-2-[(2-benzenesulfonyl-2,3,4,9-tetrahydro-1H-β-carboline-3-carbonyl)-amino]-hexanoic acid tert-butyl ester; and 6-Amino-2-{[1-methyl-2-(toluene-4-sulfonyl)-2,3,4,9-tetrahydro-1H-β-carboline-3-carbonyl]-amino}-hexanoic acid tert-butyl ester.

15. A pharmaceutical composition for increasing growth hormone secretion in a mammal, comprising an effective amount of a compound according to claim 1, and a pharmaceutical carrier.

16. A pharmaceutical composition for increasing secretion of gastrin or glucagon in a mammal, comprising an effective amount of a compound according to claim 1, and a pharmaceutical carrier.

17. A pharmaceutical composition for inhibiting the binding of somatostatin to an sst2 receptor, comprising an effective amount of a compound according to claim 1, and a pharmaceutical carrier.

18. A method for increasing growth hormone secretion in a mammal, comprising administering an effective amount of a pharmaceutical composition according to claim 15.

19. A method for increasing secretion of gastrin or glucagon in a mammal, comprising administering an effective amount of a pharmaceutical composition according to claim 16.

20. A method for decreasing somatostatin-induced inhibition of growth hormone secretion in a mammal, comprising administering an effective amount of a pharmaceutical composition according to claim 17.

21. A pharmaceutical composition according to claim 15 further comprising growth hormone releasing peptide (GHRP) or growth hormone releasing hormone (GHRH).

22. A method for increasing growth hormone secretion in a mammal, comprising administering an effective amount of a pharmaceutical composition according to claim 21.

23. A method for increasing growth hormone secretion in a mammal, comprising administering an effective amount of a pharmaceutical composition according to claim 15, and a further composition comprising growth hormone releasing peptide (GHRP) or growth hormone releasing hormone (GHRH).

24. The compound according to claim 1 wherein wherein the A' group (a) or (b) is optionally substituted by zero to five groups each independently selected from:

hydroxy, halo, amino, trifluoromethyl-, carboxy, ($C_1$-$C_6$) alkoxy-, ($C_1$-$C_6$)acyloxy-, ($C_{1-6}$)alkylamino-, (($C_1$-$C_6$)alkyl)$_2$amino-, ($C_1$-$C_6$)acylamino-, cyano, nitro, ($C_1$-$C_6$)alkyl-, ($C_2$-$C_6$)alkenyl-, ($C_2$-$C_6$) alkynyl-, ($C_1$-$C_6$)acylamino-, cyano nitro, ($C_1$-$C_6$) alkyl-, trifluoromethyl($C_1$-$C_6$)alkyl-, nitro($C_1$-$C_6$) alkyl-, ($C_1$-$C_3$)alkyl(difluoromethylene)($C_1$-$C_3$)alkyl-, ($C_1$-$C_6$)acylamino($C_1$-$C_6$)alkyl-, ($C_1$-$C_6$)alkoxy ($C_1$-$C_6$)acylamino-, amino($C_1$-$C_6$)acyl-, amino ($C_1$-$C_6$)acyl($C_1$-$C_6$)alkyl-, ($C_1$-$C_6$)alkylamino ($C_1$-$C_6$)acyl-, (($C_1$-$C_6$)alkyl)$_2$amino($C_1$-$C_6$)acyl-, ($C_3$-$C_{10}$)cycloalkyl($C_1$-$C_6$)alkyl-, ($C_1$-$C_6$)acyloxy ($C_1$-$C_6$)alkyl-, ($C_2$-$C_6$)alkoxy($C_1$-$C_6$)alkyl-, piperazinyl($C_1$-$C_6$)alkyl-, ($C_1$-$C_6$)acylamino($C_1$-$C_6$) alkyl-, ($C_6$-$C_{10}$)aryl($C_1$-$C_6$)alkoxy($C_1$-$C_6$)alkyl-, ($C_1$-$C_9$)heteroaryl($C_1$-$C_6$)alkoxy($C_1$-$C_6$)alkyl-, ($C_1$-$C_6$)alkylthio($C_1$-$C_6$)alkyl-, ($C_6$-$C_{10}$)arylthio ($C_1$-$C_6$)alkyl-, ($C_1$-$C_6$)alkylsulfinyl($C_1$-$C_6$)alkyl-, ($C_6$-$C_{10}$)arylsulfinyl($C_1$-$C_6$)alkyl-, ($C_1$-$C_6$) alkylsulfonyl($C_1$-$C_6$)alkyl-, ($C_6$-$C_{10}$)arylsulfonyl ($C_1$-$C_6$)alkyl-, amino($C_1$-$C_6$)alkyl-, ($C_1$-$C_6$) alkylamino($C_1$-$C_6$)alkyl-,($C_1$-$C_6$)alkyl (difluoromethylene)-, ($C_1$-$C_3$)alkyl(difluoromethylene)($C_1$-$C_3$)alkyl-, ($C_1$-$C_6$)alkoxy($C_1$-$C_6$) acyl-, ($C_1$-$C_6$)alkylamino($C_1$-$C_6$)acyl-, (($C_1$-$C_6$)alkyl)$_2$amino($C_1$-$C_6$)acyl-, ($C_6$-$C_{10}$)aryl-, ($C_1$-$C_9$) heteroaryl-, ($C_6$-$C_{10}$)aryl($C_1$-$C_6$)alkyl-, ($C_1$-$C_9$) heteroaryl($C_1$-$C_6$)alkyl-, ($C_6$-$C_{10}$)aryl($C_6$-$C_{10}$)aryl-, ($C_6$-$C_{10}$)aryl($C_6$-$C_{10}$)aryl($C_1$-$C_6$)alkyl-($C_3$-$C_{10}$) cycloalkyl-, ($C_3$-$C_6$)cycloalkyl($C_1$-$C_6$)alkyl-, ($C_3$-$C_{10}$)heterocycloalkyl-, ($C_3$-$C_{10}$)heterocycloalkyl ($C_1$-$C_6$)alkyl-, hydroxy($C_2$-$C_6$)alkyl-, ($C_1$-$C_6$)acyloxy ($C_2$-$C_6$)alkyl-, ($C_1$-$C_6$)alkoxy($C_2$-$C_6$)alkyl-, piperazinyl($C_1$-$C_6$)alkyl-, ($C_1$-$C_6$)acylamino($C_1$-$C_6$) alkyl-, ($C_6$-$C_{10}$)aryl($C_1$-$C_6$)alkoxy($C_1$-$C_6$)alkyl-, ($C_1$-$C_9$)heteroaryl($C_1$-$C_6$)alkoxy($C_1$-$C_6$)alkyl-, ($C_1$-$C_6$)alkylthio($C_1$-$C_6$)alkyl-, ($C_6$-$C_{10}$)arylthio ($C_1$-$C_6$)alkyl-, ($C_1$-$C_6$)alkylsulfinyl($C_1$-$C_6$)alkyl-, ($C_6$-$C_{10}$)arylsulfinyl($C_1$-$C_6$)alkyl-, ($C_1$-$C_6$) alkylsulfonyl($C_1$-$C_6$)alkyl-, ($C_6$-$C_{10}$)arylsulfonyl ($C_1$-$C_6$)alkyl-, amino($C_1$-$C_6$)alkyl-, ($C_1$-$C_6$) alkylamino($C_1$-$C_6$)alkyl-, and (($C_1$-$C_6$)alkyl)$_2$amino ($C_1$-$C_6$)alkyl-.

* * * * *